United States Patent [19]

Motoyama et al.

[11] Patent Number: 5,728,864

[45] Date of Patent: Mar. 17, 1998

[54] LIQUID CRYSTAL COMPOUND HAVING FERRIELECTRIC PHASE AND LIQUID CRYSTAL COMPOSITION

[75] Inventors: Yuki Motoyama; Tomoyuki Yui; Masahiro Johno; Maki Ito; Takahiro Matsumoto; Hiroshi Mineta, all of Tsukuba, Japan

[73] Assignee: Mitsubishi Gas Chemical Company, Inc., Tokyo, Japan

[21] Appl. No.: 631,092

[22] Filed: Apr. 12, 1996

[30] Foreign Application Priority Data

Apr. 14, 1995 [JP] Japan .................................. 7-089207
May 19, 1995 [JP] Japan .................................. 7-121679
May 19, 1995 [JP] Japan .................................. 7-121680

[51] Int. Cl.$^6$ .................. C07C 69/76; C09K 19/34; C09K 19/30; C09K 19/12; C09K 19/20; C09K 19/22

[52] U.S. Cl. .................. 560/59; 560/9; 560/10; 560/17; 560/18; 560/20; 560/21; 560/22; 560/23; 560/35; 560/55; 560/61; 560/62; 560/64; 560/65; 560/100; 560/102; 252/299.64

[58] Field of Search .................. 560/8, 9, 10, 17, 560/18, 20, 21, 22, 23, 35, 59, 61, 62, 73, 64, 65, 55, 100, 102; 252/299.64

[56] References Cited

U.S. PATENT DOCUMENTS 4,921,632  5/1990  Nakamura et al. .................. 252/299.1

FOREIGN PATENT DOCUMENTS

| 64-3154 | 1/1989 | Japan . |
|---|---|---|
| 5150257 | 6/1993 | Japan . |
| 5249502 | 9/1993 | Japan . |
| 6-95080 | 4/1994 | Japan . |
| 6271852 | 9/1994 | Japan . |

OTHER PUBLICATIONS

Inui, et al., "Thresholdless Antiferroelectricity...", Journal of Materials Chemistry, 1996, 6(4), 671–673.

Inui, et al., "Synthesis And Physical..." Ferroelectrics, vol. 148, No. 1-4, 1993, pp. 79–84.

Abstract of Japanese Laid–Open Patent Appln. Publication No. 6-145111 (May 24, 1994).

Abstract of Japanese Laid–Open Patent Appln. Publication No. 7-242601 (Sep. 19, 1995).

Abstract of Japanese Laid–Open Patent Appln. Publication No. 7-252479 (Oct. 3, 1995).

Abstract of Japanese Laid–Open Patent Appln. Publication No. 8-3561 (Jan. 9, 1996).

Gorecka, et al. "Molecular Orientational Structures in..." Jap. J. App. Phys., vol. 29, No. 1, Jan. 1990, pp. 131–137.

Nito, et al. "TFT–driven Monostable Ferroelectric...", SID '94, Preprint p. 48 (1994).

Primary Examiner—Floyd D. Higel
Attorney, Agent, or Firm—Sherman and Shalloway

[57] ABSTRACT

A liquid crystal compound of the formula (1)

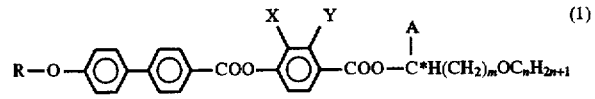

wherein

R is a linear alkyl group having 6 to 12 carbon atoms, both X and Y are hydrogen atoms or one of X and Y is a fluorine atom and the other is a hydrogen atom, A is —$CF_3$ or —$C_2F_5$, m is an integer of 2 to 4, n is an integer of 2 to 4, and C* is an asymmetric carbon, having a ferrielectric phase in its phase sequence, or a ferrielectric liquid crystal composition containing the liquid crystal compound of the formula (1) having a ferrielectric phase, may be injected between substrates provided with nonlinear active elements, such as thin film transistors or diodes formed on each pixel, to form an active matrix liquid crystal display device.

28 Claims, 4 Drawing Sheets

LIQUID CRYSTAL COMPOUND HAVING FERRIELECTRIC PHASE AND LIQUID CRYSTAL COMPOSITION

FIELD OF THE INVENTION

The present invention relates to a novel liquid crystal compound having a ferrielectric phase suitable use in an active matrix liquid crystal display in which a liquid crystal is driven for each pixel, and use thereof.

PRIOR ART OF THE INVENTION

A liquid crystal display device (LCD) has been widely applied to portable devices as a flat panel display as a substitute for a conventional cathode-ray tube display. With a recent extension of the functions of a personal computer and a word processor and with a recent increase in the volume of information to be processed, LCD is as well required to have enhanced functions such as an increased display capacity, full-color display, a wide viewing angle, rapid response and a high contrast.

As a liquid crystal display mode (liquid crystal driving method) for complying with the above requirements, there has been proposed and used an active matrix (AM) display device in which a thin film transistor (TFT) or a diode (MIM) is formed for each pixel and a liquid crystal of each pixel is independently driven.

The method using the above AM display device has problems in the difficulty in decreasing the cost due to low yields and the difficulty in forming a large-sized screen, but owing to its high display quality, it is about to exceed a conventionally main-stream STN display mode and catch up with a CRT display mode at a great rate.

However, the AM display device has the following problems due to the use of a TN (twisted nematic) liquid crystal as a liquid crystal material.

(1) The response speed of a TN liquid crystal is generally low (several tens ms.) since it is a nematic liquid crystal, and no good display quality can be obtained when used for video frame rate display.

(2) The viewing angle of a TN liquid crystal is narrow since the display uses a twisted state (twisted alignment) of a liquid crystal molecule. In realization of gray scaling in particular, the viewing angle is sharply narrowed. In other words, the contrast ratio and color are altered in some viewing angles.

For overcoming the above problem, AM display devices for which a ferroelectric liquid crystal or an anti-ferroelectric liquid crystal is adapted have been proposed in recent years (see for example, Japanese Laid-open Patent Publications Nos. 5-249502, 5-150257 and 6-95080). However, these liquid crystals have the following problems (1) and (2), and it is therefore difficult to put them into practical use.

(1) A ferroelectric liquid crystal has spontaneous polarization, and an image sticking on a screen is liable to take place due to a constant presence of the spontaneous polarization, so that driving is difficult. Further, a ferroelectric liquid crystal can switch only two-values (black and white), in principle and it is therefore very difficult to realize gray scaling.

For realizing the gray-scaling display, particular technology is required (e.g., ferroelectric liquid crystal device using "monostable"; Keiichi Nito, et al., SID '94, Preprint P. 48), and it is required to develop a efficiency practical technique.

(2) An anti-ferroelectric liquid crystal is free from the image sticking problem referred to above since no permanent spontaneous polarization is present. However, an AM requires a liquid crystal material which can be driven at a voltage of 10 V or lower, and it is difficult to drive a display device of the anti-ferroelectric liquid crystal at a low voltage since the anti-ferroelectric liquid crystal generally has a high threshold voltage.

Further, an anti-ferroelectric liquid crystal has another problem in that gray-scaling is difficult to realize due to hysterisis in optical response.

It is an object of the present invention to provide a novel material which can overcome the above problems and can be suitably adapted for AM driving, and a liquid crystal compound having a ferrielectric phase can be considered to be one of such materials.

A liquid crystal compound having a ferrielectric phase (=$SC\gamma^*$) was first found in 4-(4-octyloxyphenyl)benzoic acid-4-(1-methylheptyloxycarbonyl)phenyl (called "MHPOBC" for short) in 1989 (Japanese Journal of Applied Physics, Vol. 29, No. 1, 1990, pages L131–137).

MHPOBC has the formula of

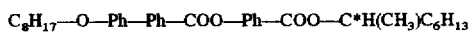

in which Ph is 1,4-phenylene, C* is asymmetric carbon and each of $C_8$ alkyl and $C_6$ alkyl is linear, and its phase sequence is as follows.

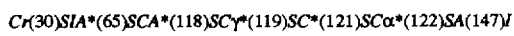

in which Cr is a crystal phase, SIA* is a chiral smectic IA phase, SCA* is a chiral smectic CA phase (anti-ferroelectric phase), SC$\gamma$* is a chiral smectic C$\gamma$ phase (ferrielectric phase), SC* is a chiral smectic C phase (ferroelectric phase), SC$\alpha$* is a chiral smectic C$\alpha$ phase, SA is a smectic A phase, I is an isotropic phase, and parenthesized figures show phase transition temperatures (°C.).

BRIEF DESCRIPTION OF DRAWINGS

For explaining the state of a liquid crystal in a ferrielectric phase, FIG. 1 shows a molecular arrangement state in a ferrielectric phase, and FIG. 2 shows an optical response of a ferrielectric phase to a triangular wave.

The ferrielectric phase has a molecular arrangement FI(+) (when charged voltage is positive) or a molecular arrangement FI(−) (when charged voltage is negative). In a state where no electric field is present, it is assumed that FI(+) and FI(−) are co-present since FI(+) and FI(−) are equivalent.

Figure 1:
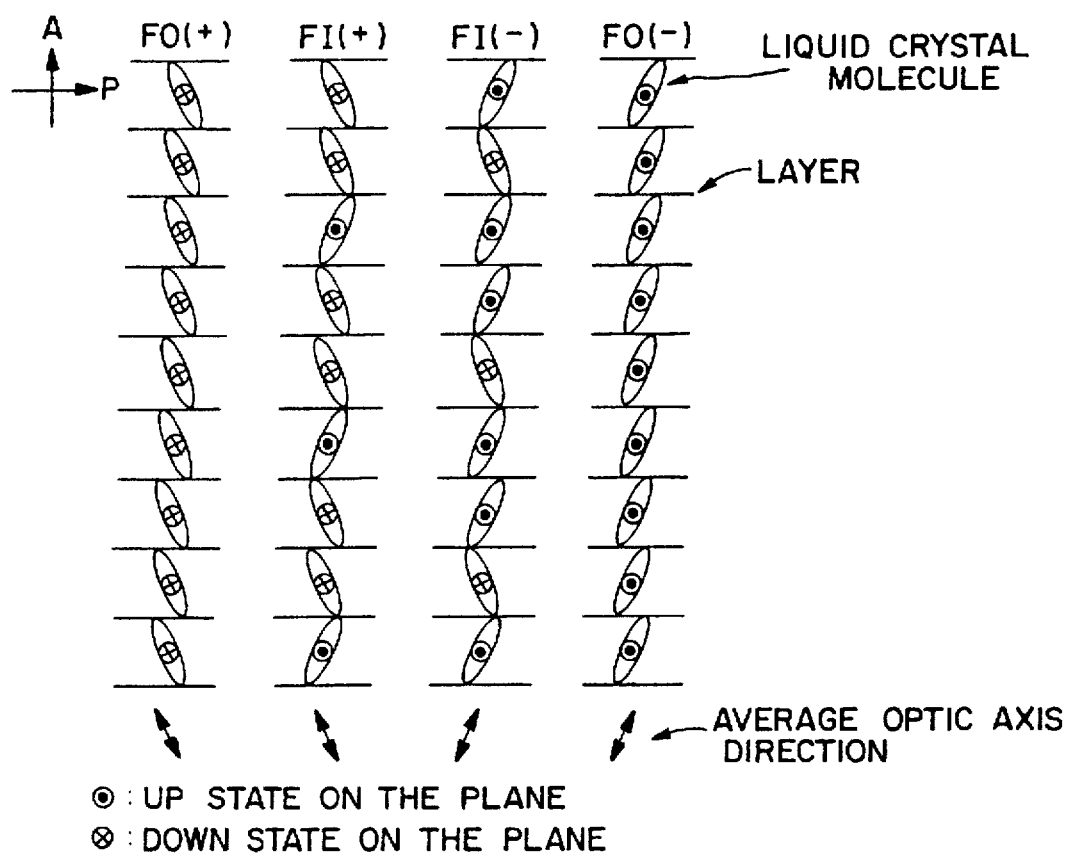
FIG. 1 shows the molecular arrangement of a ferrielectric phase, in which FI(+) and FI(−) show ferrielectric state, and FO(+) and FO(−) show ferroelectric state.

An average optic axis is therefore in a layer normal, and a dark state is brought under the condition of a polarizer shown in FIG. 1.

Figure 2:
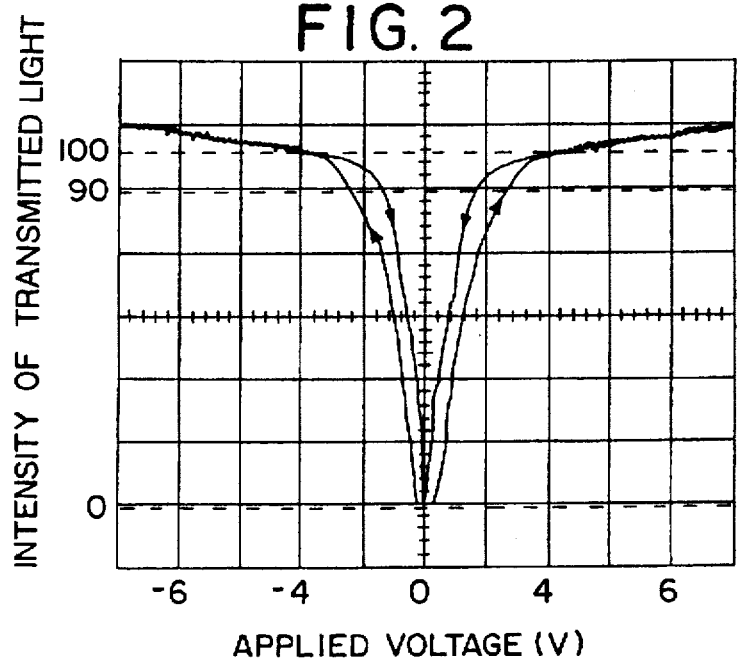
FIG. 2 shows an optical response of the ferrielectric phase of MHPOBC to triangular wave voltage.

The above state corresponds to a site where a charged voltage is 0 and the intensity of transmitted light is 0 in FIG. 2.

Further, each of FI(+) and FI(−) has spontaneous polarization as is clear in molecular arrangement states, and when these are co-present, the spontaneous polarizations are canceled, which causes an average spontaneous polarization of zero. Like an anti-ferroelectric phase, the ferrielectric phase is therefore free from an image sticking phenomenon.

As an electric field is applied to a ferrielectric phase, a domain having an extinguished position appears at a voltage lower than that at which a ferroelectric state is reached. This domain shows that a ferrielectric phase has an optic axis in a direction tilted apart from a layer normal although it is not so tilted as that in a ferroelectric state.

The above intermediate state is considered to be FI(+) or FI(−).

In the above case, not a continuous change but a stepwise change in the intensity of transmitted light could have been observed between voltages 0V and 4V in FIG. 2. In FIG. 2, however, a continuous intensity of transmitted light was observed. This is presumably because the threshold voltage of FI(+)→FO(+) or FI(−)→FO(−) is not clear.

In the present invention, a liquid crystal phase in which the above intermediate state is always observed refers to a ferrielectric phase, and a liquid crystal compound having said phase refers to a liquid crystal compound having a ferrielectric phase.

When the charged voltage is further increased, the ferrielectric phase causes phase transition to a ferroelectric phase FO(+) or FO(−) that is a stabilized state, depending upon a direction of an electric field. That is, in FIG. 2, a phase in which the intensity of transmitted light is brought into a saturated state (flat portions on right and left sides) is FO(+) or FO(−).

It is seen in FIG. 1 that the above ferroelectric state FO(+) or FO(−) causes a greater spontaneous polarization than the ferrielectric state FI(+) or FI(−).

As explained above, the ferrielectric phase can be used as follows; A state where FI(+) and FI(−) are co-present is "dark", and ferroelectric states FO(+) and FO(−) are "bright".

A conventional ferroelectric liquid crystal permits switching between FO(+) and FO(−), while a ferrielectric phase has a major characteristic feature in that it permits switching among four states, FI(+), FO(+), FO(−) and FI(−).

Meanwhile, the display device principle of each liquid crystal uses birefringence of liquid crystal and hence, a display device of which the viewing angle dependency is small can be fabricated.

As shown in FIG. 2, a ferrielectric phase has a small difference between the voltage required to change from a ferrielectric state to a ferroelectric state and the voltage required to change from a ferroelectric state to a ferrielectric state. That is, a ferrielectric phase has a strong tendency that the width of its hysterisis is narrow, and the ferrielectric phase is characteristically suitable for AM driving and a gray-scaling can be realized in AM driving.

Further, in a change based on voltage, a ferrielectric phase has a tendency that the threshold voltage which is a voltage for a change from a ferrielectric state to a ferroelectric state is smaller than that of an anti-ferroelectric phase, which also proves that the ferrielectric phase is a liquid crystal phase suitable for AM driving.

However, few liquid crystal compounds having a ferrielectric phase have been synthesized, and any of known liquid crystal compounds having a ferrielectric phase are not satisfactory in hysterisis and threshold voltage when the application thereof to an AM driven device is considered.

The present invention provides, therefore, a novel liquid crystal compound having a ferrielectric phase suitable for AM driving.

According to the present invention, there is provided a liquid crystal compound of the formula (1) having a ferrielectric phase in its phase sequence.

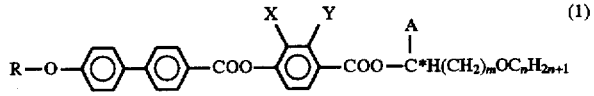

wherein R is a linear alkyl group having 6 to 12 carbon atoms, both X and Y are hydrogen atoms or one of X and Y is a fluorine atom and the other is a hydrogen atom, A is —$CF_3$ or —$C_2F_5$, m is an integer of 2 to 4, n is an integer of 2 to 4, and C* is an asymmetric carbon.

According to the present invention, further, there is provided a ferrielectric liquid crystal composition containing the liquid crystal compound having a ferrielectric phase, represented by the above formula (1).

Further, according to the present invention, there is provided an active matrix liquid crystal display device formed by injecting the above liquid crystal compound having a ferrielectric phase or the above ferrielectric liquid crystal composition containing the above compound between substrates provided with non-linear active matrix elements such as thin film transistors or diodes which are formed on each pixel.

In the present invention, the liquid crystal compound of the general formula (1) in which A is $CF_3$ is preferably a liquid crystal compound of which the liquid crystal phase sequence is formed of crystal phase (Cr)—ferrielectric phase (SC$\gamma$*)—smectic A phase (SA) or unidentified liquid crystal phase (SX)—isotropic phase (I).

Further, the liquid crystal compound of the general formula (1) in which A is —$CF_3$, X is H, Y is F, m is 4, R is a linear alkyl group having 6 to 12 carbon atoms and n is an integer of 2 to 4 (Examples 13 to 21); A is —$CF_3$, X is H, Y is H, m is 4, R is a linear alkyl group having 7 to 12 carbon atoms and n is an integer of 2 to 4 (Examples 22 to 29); A is —$CF_3$, X is F, Y is H, m is 4, R is a linear alkyl group having 8 to 12 carbon atoms and n is an integer of 2 to 4 (Examples 30 to 34); the liquid crystal compound of the general formula (1) in which A is —$CF_3$, m is 3, R is a linear alkyl group having 9 to 12 carbon atoms and n is an integer of 2 to 4 (Examples 1 to 12); and the liquid crystal compound of the general formula (1) in which A is —$CF_3$, m is 2 and R is a linear alkyl group having 8 or 9 carbon atoms are preferred liquid crystal compounds, and in particular, the liquid crystal compound of the general formula (1) in which A is —$CF_3$, m is 2, R is a linear alkyl group having 8 or 9 carbon atoms and n is 2 (Examples 35 to 37) gives a preferred liquid crystal compound having a ferrielectric phase.

The liquid crystal compound of the general formula (1) in which A is —$C_2F_5$, R is a linear alkyl group having 8 to 11 carbon atoms and n is an integer of 2 to 4 gives liquid crystal compounds having a ferrielectric phase.

A back-light is generally installed in an AM-driven display device so that a temperature of the display device is at least about 40° C. In the liquid crystal compound having a ferrielectric phase provided by the present invention, therefore, it is suitable that the phase transition temperature on the high temperature side should be at least 40° C., preferably at least 50° C.

However, in actual practice, a ferrielectric liquid crystal is used alone in no case, and various other materials are incorporated for optimizing physical properties. As a result, a liquid crystal compound having a transition temperature of about 30° C. on the high temperature side can be adequately used, since the transition temperature of a composition can be increased by incorporating a material having a higher transition temperature.

On the other hand, the temperature range of the ferrielectric phase is an important factor since it is concerned with a driving temperature range. The temperature range of a material for practical use can be increased by incorporating other material, while the temperature range of the ferrielectric phase is preferably at least 10° C.

The driving voltage of a practically used AM-driven display device is 10 V or lower, and the driving voltage can be greatly decreased further. Generally, a ferrielectric liquid crystal has a low threshold voltage, and it can be easily driven at a low voltage. However, the threshold voltage of transition from a ferrielectric state to a ferroelectric state is preferably not more than 5V/μm (cell thickness), the most preferably not more than 3V/μm.

The ferrielectric liquid crystal compound of the general formula (1), provided by The present invention, can be used as a ferrielectric liquid crystal composition, and the content of the ferrielectric liquid crystal compound having a ferrielectric phase in the composition is 95 to 50 mol %, preferably 90 to 60 mol%, particularly preferably 90 to 70 mol %. The ferrielectric liquid crystal composition preferably has at least a ferrielectric phase in a temperature range of 0° to 40° C. and at least a smectic A phase on the high temperature side of the ferrielectric phase.

In particular, the above ferrielectric liquid crystal composition preferably further contains a phenyl ester compound of the following general formula (2).

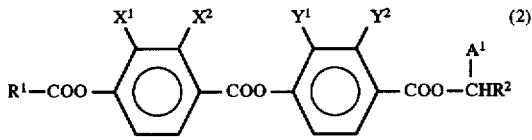

wherein $R^1$ is a linear alkyl group having 5 to 12 carbon atoms, $R^2$ is a linear alkyl group having 1 to 15 carbon atoms, both of $X^1$ and $X^2$ are hydrogen atoms or one of $X^1$ and $X^2$ is a fluorine atom and the other is a hydrogen atom, both of $Y^1$ and $Y^2$ are hydrogen atoms or one of $Y^1$ and $Y^2$ is a fluorine atom and the other is a hydrogen atom, $A^1$ is a hydrogen atom or —$CH_3$.

The compound of the general formula (2) used in the present invention is preferably as follows. A compound of the general formula, which has a smectic A phase; a compound of the general formula (2) in which $R^1$ is a linear alkyl group having 8 to 12 carbon atoms; a compound of the general formula (2) in which $A^1$ is a hydrogen atom and $R^2$ is a linear alkyl group having 2 to 10 carbon atoms; an optically active compound of the general formula (2) in which $A^1$ is —$CH_3$ and $R^2$ is a linear alkyl group having 3 to 8 carbon atoms.

The liquid crystal compound having a ferrielectric phase or the ferrielectric liquid crystal composition containing the above compound can give an active matrix liquid crystal display device having a high display quality when injected between substrates provided with non-linear active elements such as thin film transistors or diodes which are formed on each pixel. And the active matrix liquid crystal device can be used as one in which the driving of a liquid crystal by a voltage with non-linear active matrix elements is performed by switching among two ferrielectric states, two ferroelectric states and intermediate states therebetween.

An optically active alcohol used in the present invention can be easily produced by the method disclosed by the present inventors (for example, Japanese Laid-open Patent Publication No. 4-983).

The method of the production thereof is outlined as follows.

 (a)

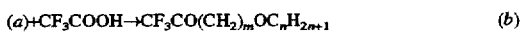 (b)

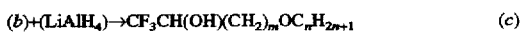 (c)

 (d)

 (e)

The above method of producing the optically active alcohol are briefly explained as follows.

(a) A Grignard reagent of alkyloxy bromide is prepared.
(b) A ketone is prepared by reacting the Grignard reagent and trifluoroacetic acid. (c) A racemic alcohol is prepared by reducing the ketone. (d) The racemic alcohol is acetylated (e) Acetate is asymmetrically hydrolyzed with lipase, whereby an R-form optically active alcohol as an end product and an S-form acetate are obtained.

The liquid crystal compound having a ferrielectric phase, provided by the present invention, can be easily produced by, for example, the method disclosed by the present inventors (Japanese Laid-open Patent Publication No. 3-292388).

The above method is outlined as follows.

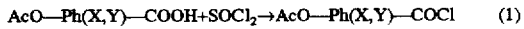 (1)

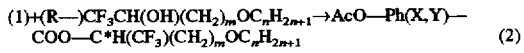 (2)

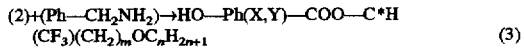 (3)

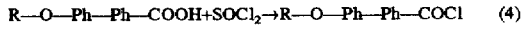 (4)

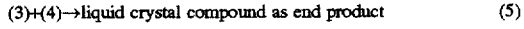 (5)

In the above reaction scheme, Ph is a 1,4-phenylene group, Ph(X,Y) is a 1,4-phenylene group in which a fluorine atom may be substituted on the 2- or 3-position (X o Y in the general formula 1), and C* is an asymmetric carbon.

The above production method is briefly outlined as follows.

(1) p-Acetoxybenzoic acid is chlorinated with thionyl chloride.
(2) An ester is formed by reacting the chloride (1) and an optically active alcohol.
(3) The ester (2) is deacetylated.
(4) 4'-Alkyloxybiphenyl-4-carboxylic acid is chlorinated.
(5) A liquid crystal is produced by reacting the phenol (3) and the chloride (4).

EXAMPLES

The present invention will be explained more in detail with reference to Examples hereinafter. However, the present invention shall not be limited to these Examples. In the following Examples, the chemical formulas of the liquid crystal compounds (E1 to E40) are shown in pages 29 to 36.

Example 1

Preparation of 3-fluoro-4-(1-trifluoromethyl-4-ethoxy-butyloxycarbonyl)phenyl=4'-n-nonyloxybiphenyl-4-carboxylate (compound of the general formula (1) in which $R=C_9H_{19}$, $X=H$, $Y=F$, $A=CF_3$, $m=3$ and $n=2$   (E1))

(1) Preparation of 4-(4'-n-nonyloxy)biphenylcarboxylic acid 10.5 Grams of 4-(4'-hydroxy)biphenylcarboxylic acid and 14.0 g of n-nonyl bromide were dissolved in a mixed solvent of 1,500 ml of ethanol with 200 ml of water, and the mixture was allowed to react under reflux for 10 hours. Further, 500 ml of water was added, and the mixture was stirred for 3 hours.

After the completion of the reaction, the reaction mixture was acidified by adding concentrated hydrochloric acid, and the solvent was distilled off in an amount of 500 ml. The residue was cooled to room temperature to give a white solid. The white solid was fully washed with water and recrystallized from chloroform to give 11.4 g of a white crystal.

(2) Preparation of 4-acetoxy-2-fluorobenzoic acid 4.3 Grams of 2-fluoro-4-hydroxybenzoic acid and 8.4 g of acetic anhydride were placed in a two-necked flask and mixed. While the mixture was cooled with water, 5 drops of sulfuric acid was added. After the heat generation ended, the mixture was heated at 80° C. for 30 minutes. Then, the reaction mixture was poured into cold water, and precipitated crystal was recovered by filtration. The crystal was dried under vacuum and used in a subsequent step. The yield of the crystal was 4.7 g.

(3) Preparation of 4-acetoxy-2-fluoro-1-(1-trifluoromethyl-4-ethoxy-butyloxycarbonyl)benzene 1.2 Grams of 4-acetoxy-2-fluorobenzoic acid was added to 7 ml of thionyl chloride, and the mixture was allowed to react under reflux for 5 hours. Then, excessive thionyl chloride was distilled off, and then a mixture containing 1 ml of pyridine, 4 ml of dry ether and 0.9 g of R-(+)-5-ethoxy-1,1,1-trifluoro-2-pentanol was dropwise added.

After the addition, the mixture was stirred at room temperature for 1 day and diluted with 200 ml of ether, and an organic layer was consecutively washed with diluted hydrochloric acid, with a 1N sodium hydroxide aqueous solution and with water, and dried over magnesium sulfate. The solvent was distilled off, and the residue was purified by silica gel column chromatography using hexane/ethyl acetate as a solvent to give 1.5 g of the end product.

(4) Preparation of 4-hydroxy-2-fluoro-(1-trifluoromethyl-4-ethoxy-butyloxy)benzene 1.0 Gram of the compound obtained in the above (3) was dissolved in 30 ml of water, and 3 g of benzylamine was dropwise added. Further, the mixture was stirred at room temperature for 1 day, diluted with 300 ml of ether, consecutively washed with diluted hydrochloric acid and with water, and then dried over magnesium sulfate.

The solvent was distilled off, and the residue was isolated and purified by silica gel column chromatography to give 0.7 g of the end product.

(5) Preparation of 3-fluoro-4-(1-trifluoromethyl-4-ethoxy-butyloxycarbonylphenyl)- 4'-n-nonyloxybiphenyl-4-carboxylate Thionyl chloride in an amount of 10 ml was added to 0.9 g of the compound obtained in the above (1), and the mixture was refluxed under heat for 10 hours. Excessive thionyl chloride was distilled off, 10 ml of pyridine and 25 ml of toluene were added. Then, a solution of 0.7 g of the compound obtained in the above (4) in 25 ml of benzene was dropwise added, and the mixture was allowed to react at room temperature for 10 hours. After the completion of the reaction, the reaction mixture was diluted with 300 m of ether, and consecutively washed with diluted hydrochloric acid, with a 1N sodium carbonate aqueous solution and with water, and an organic layer was dried over magnesium sulfate.

Then, the solvent was distilled off, and a crude product was isolated by silica gel column chromatography and then recrystallized from ethanol to give 0.7 g of a liquid crystal as an end product (to be referred to as "E1" hereinafter).

Table 1 shows 1H-NMR spectrum data of E1 and the chemical formula thereof is shown below (page 29).

Phases were identified by texture observation, conoscopic figure observation, DSC (differential scanning calorimeter) measurement and finding of a domain having an extinguished position between a layer normal and an optic axis in a ferroelectric state (observation of a intermediate state FI(±)).

The observation of a conoscopic figure is effective means of identifying a ferrielectric phase. The conoscopic figure observation was conducted according to a piece of literature (J. Appl. Phys. 31, 793 (1992)). The phase sequence of the compound in this Example was determined on the basis of the texture observation, the conoscopic figure observation and DSC measurement by general parallel alignment cell, and the observation of an intermediate state FI(±), and it was found that the compound in this Example was a ferrielectric liquid crystal. Table 4 shows the results.

The above-obtained ferrielectric liquid crystal was studied for an optical response. A cell was prepared in the following procedures.

A pair of glass substrates with insulating film (SiO$_2$, thickness 50 nm) and ITO electrodes were coated with polyimide (thickness about 80 nm), and one of the pair of the glass substrates was rubbed. The glass substrates were attached to each other through a spacer having a particle diameter of 1.6 μm to form a test cell. The cell thickness was 2 μm. The above liquid crystal was heated until it had an isotropic phase, and the liquid crystal was injected into the test cell by capillarity. Then, the liquid crystal was gradually cooled at a rate of 1° C./minute to align the liquid crystal in parallel.

Figure 3:
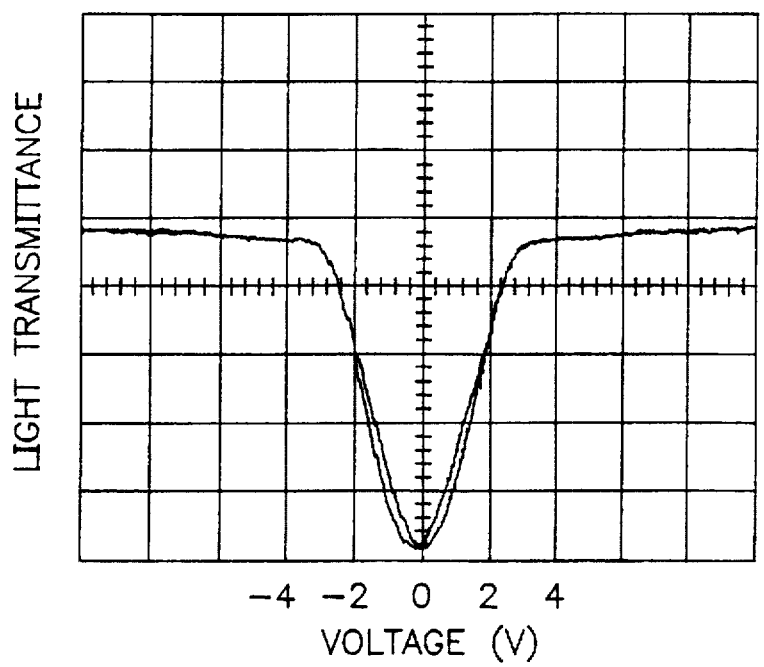
FIG. 3 shows an optical response of the compound obtained in Example 1 to triangular wave voltage at 101° C.
Figure 4:
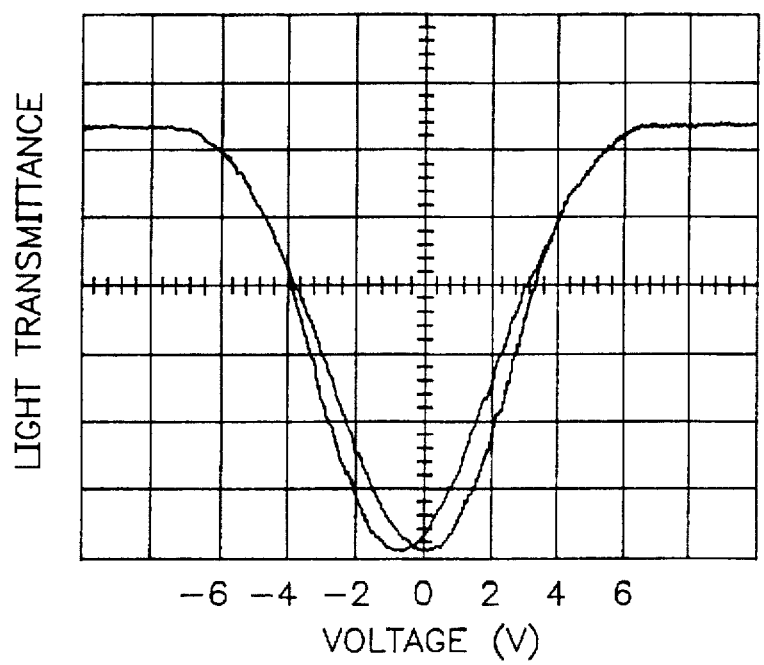
FIG. 4 shows an optical response of the compound obtained in Example 1 to triangular wave voltage at 60° C.
Figure 5:
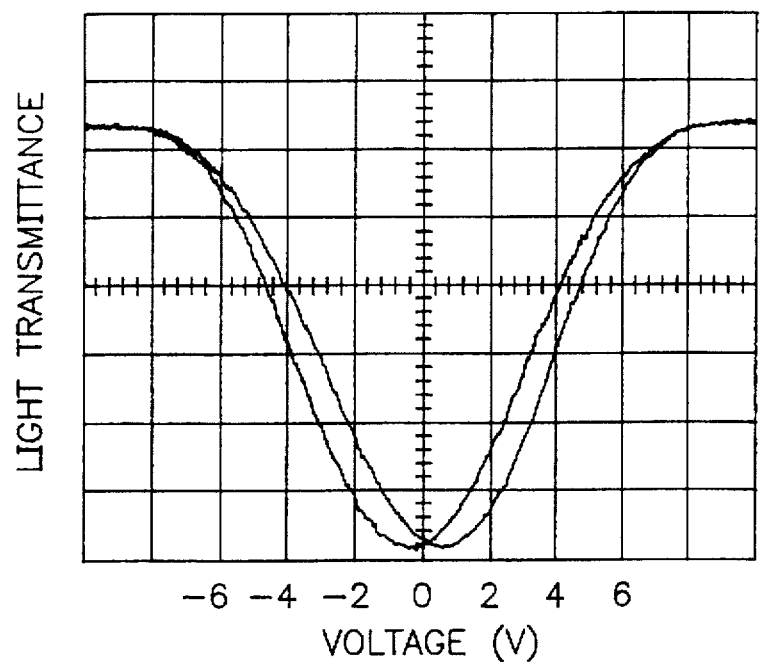
FIG. 5 shows an optical response of the compound obtained in Example 1 to triangular wave voltage at 40° C.

Then, the test cell was driven by charging a triangular wave voltage of ±20V, 1Hz to the test cell at each temperature of 101° C., 60° C. and 40° C. to study a change in transmitted light. FIGS. 3, 4 and 5 show the results. The threshold voltage (voltage at which the transmitted light intensity became 90%) at each temperature was not more than 3 V/μm, and the test cell showed almost no hysterisis in optical response. Further, when the charged voltage was 0, a good dark state was obtained.

Examples 2–4

Preparation of (i) 3-fluoro-4-(1-trifluoromethyl-4-ethoxy-butyloxycarbonyl)phenyl=4'-n-decyloxybiphenyl-4-carboxylate (compound of the general formula (1) in which $R=C_{10}H_{21}$, $X=H$, $Y=F$, $A=CF_3$, $m=3$ and $n=2$)   (E2)

(ii) 3-fluoro-4-(1-trifluoromethyl-4-ethoxy-butyloxycarbonyl)phenyl=4'-n-undecyloxybiphenyl-4-carboxylate (compound of the general formula (1) in which R=C₁₁H₂₃, X=H, Y=F, A=CF₃, m=3 and n=2)   (E3)

and (iii) 3-fluoro-4-(1-trifluoromethyl-4-ethoxy-
butyloxycarbonyl)phenyl=4'-n-dodecyloxybiphenyl-4-
carboxylate (compound of the general formula (1) in
which R=C₁₂H₂₅, X=H, Y=F, A=CF₃, m=3 and n=2)   (E4)

End products were obtained in the same manner as in Example 1 except that 4-(4'-n-nonyloxy)biphenylcarboxylic acid was replaced with 4-(4'-n-decyloxy)biphenylcarboxylic acid (Example 2), 4-(4'-n-undecyloxy)biphenylcarboxylic acid (Example 3) or 4-(4'-n-dodecyloxy)biphenylcarboxylic acid (Example 4).

The end products were measured for physical properties in the same manner as in Example 1, and the NMR of the compounds and the measurement results are shown in Tables 1 and 4.

Examples 5 and 6

Preparation of
3-fluoro-4-(1-trifluoromethyl-4-propyloxy-
butyloxycarbonyl)phenyl=4'-n-nonyloxybiphenyl-4-
carboxylate (compound of the general formula (1) in
which R=C₉H₁₉, X=H, Y=F, A=CF₃, m=3 and n=3)   (E5)

and 3-fluoro-4-(1-trifluoromethyl-4-butoxy-
butyloxycarbonyl)phenyl=4'-n-nonyloxybiphenyl-4-
carboxylate (compound of the general formula (1) in
which R=C₉H₁₉, X=H, Y=F, A=CF₃, m=3 and n=4)   and (E6)

End products were obtained in the same manner as in Example 1 except that R-(+)-5-ethoxy-1,1,1-trifluoro-2-pentanol was replaced with R-(+)-5-propyloxy-1,1,1-trifluoro-2-pentanol (Example 5) or R-(+)-5-buthoxy-1,1,1-tritrifluoro-2-pentanol (Example 6). The NMR of the compounds and the results are shown in Tables 1 and 4.

Example 7

Preparation of 4-(1-trifluoromethyl-4-ethoxy-
butyloxycarbonyl)phenyl=4'-n-nonyloxybiphenyl-4-
carboxylate (compound of the general formula (1) in which R=C₉H₁₉, X=H, Y=H, A=CF₃, m=3 and n=2)   (E7)

An end product was obtained in the same manner as in Example 1 except that 2-fluoro-4-acetoxybenzoic acid was replaced with 4-acetoxybenzoic acid.

The obtained compound was measured for physical properties in the same manner as in Example 1, and the NMR of the compound and the results are shown in Tables 1 and 4.

Examples 8 and 9

Preparation of
4-(1-trifluoromethyl-4-propyloxy-butyloxycarbonyl)
phenyl=4'-n-nonyloxybiphenyl-4-carboxylate
(compound of the general formula (1) in which R=C₉H₁₉, X=H; Y=H, A=CF₃, m=3 and n=3)   (E8)

and 4-(1-trifluoromethyl-4-butyloxy-butyloxycarbonyl)
phenyl=4'-n-nonyloxybiphenyl-4-carboxylate
(compound of the general formula (1) in which R=C₉H₁₉, X=H, Y=H, A=CF₃, m=3 and n=4)   (E9)

End products were obtained in the same manner as in Example 7 except that R-(+)-5-ethoxy-1,1,1-trifluoro-2-pentanol was replaced with R-(+)-5-propyloxy-1,1,1-trifluoro-2-pentanol (Example 8) or R-(+)-5-buthoxy-1,1,1-trifluoro-2-pentanol (Example 9), and the NMR of the compounds and the results are shown in Tables 1 and 4.

Example 10

Preparation of 2-fluoro-4-(1-trifluoromethyl-4-ethoxy-
butyloxycarbonyl)phenyl=4'-n-nonyloxybiphenyl-4-
carboxylate (compound of the general formula (1) in which R=C₉H₁₉, X=F, Y=H, A=CF₃, m=3 and n=2)   (E10)

An end product was obtained in the same manner as in Example 1 except that 2-fluoro-4-acetoxybenzoic acid was replaced with 3-fluoro-4-acetoxybenzoic acid.

The obtained compound was measured for physical properties in the same manner as in Example 1, and the NMR of the compounds and the results are shown in Tables 1 and 4.

Examples 11 and 12

Preparation of
2-fluoro-4-(1-trifluoromethyl-4-propyloxy-
butyloxycarbonyl)phenyl=4'-n-nonyloxybiphenyl-4-
carboxylate (compound of the general formula (1) in
which R=C₉H₁₉, X=F, Y=H, A=CF₃, m=3 and n=3)   (E11)

and 2-fluoro-4-(1-trifluoromethyl-4-butyloxy-
butyloxycarbonyl)phenyl=4'-n-nonyloxybiphenyl-4-
carboxylate (compound of the general formula (1) in
which R=C₉H₁₉, X=F, Y=H, A=CF₃, m=3 and n=4)   (E12)

End products were obtained in the same manner as in Example 10 except that R-(+)-5-ethoxy-1,1,1-trifluoro-2-pentanol was replaced with R-(+)-5-propyloxy-1,1,1-trifluoro-2-pentanol (Example 11) or R-(+)-5-buthoxy-1,1,1-trifluoro-2-pentanol (Example 12), and the NMR of the compounds and the results are shown in Tables 1 and 4.

Comparative Examples 1 and 2

Preparation of
3-fluoro-4-(1-trifluoromethyl-4-ethoxy-
butyloxycarbonyl)phenyl=4'-n-heptyloxybiphenyl-4-
carboxylate (compound of the general formula (1) in
which R=C₇H₁₅, X=H, Y=F, A=CF₃, m=3 and n=2)   (CE1), and 3-fluoro-4-(1-trifluoromethyl-4-ethoxy-
butyloxycarbonyl)phenyl=4'-n-octyloxybiphenyl-4-
carboxylate (compound of the general formula (1) in
which R=C₈H₁₇, X=H, Y=F, A=CF₃, m=3 and n=2)   (CE2).

End products were obtained in the same manner as in Example 1 except that 4-(4'-n-nonyloxy)biphenylcarboxylic acid was replaced with 4-(4'-n-heptyloxy) biphenylcarboxylic acid (Comparative Example 1) or 4-(4'-n-octyloxy)biphenylcarboxylic acid (Comparative Example 2). The NMR of the compounds and the results are shown in Tables 1 and 4.

Figure 6:
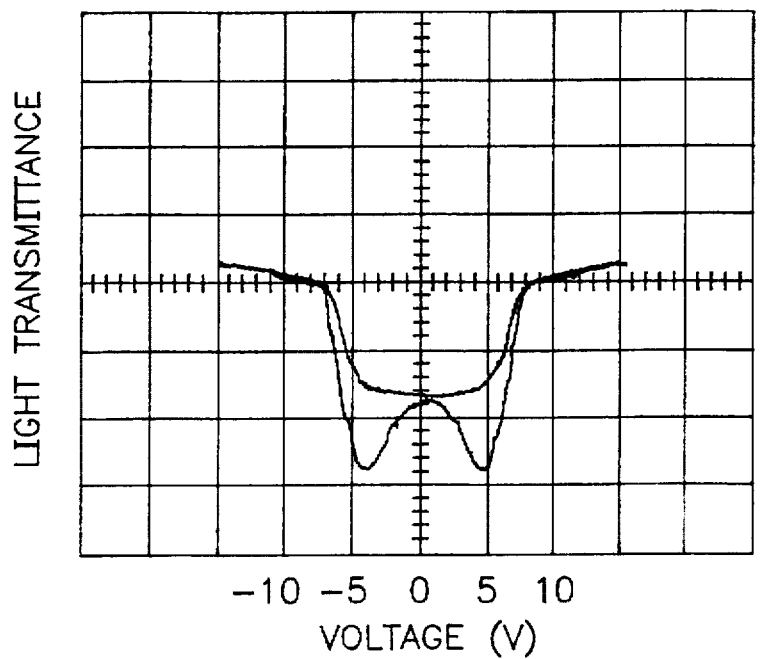
FIG. 6 shows an optical response of the compound obtained in Comparative Example 2 to triangular wave voltage at 108° C.
Figure 7:
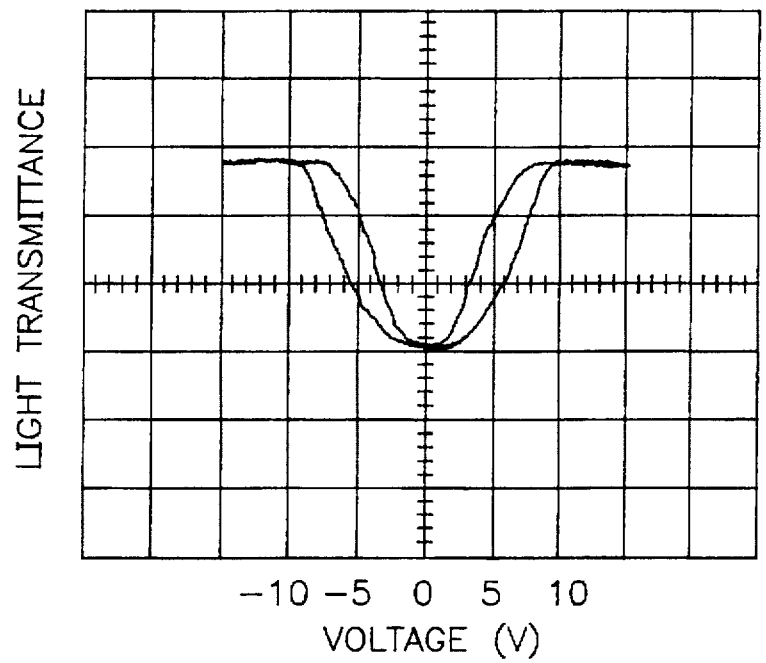
FIG. 7 shows an optical response of the compound obtained in Comparative Example 2 to triangular wave voltage at 80° C.
Figure 8:
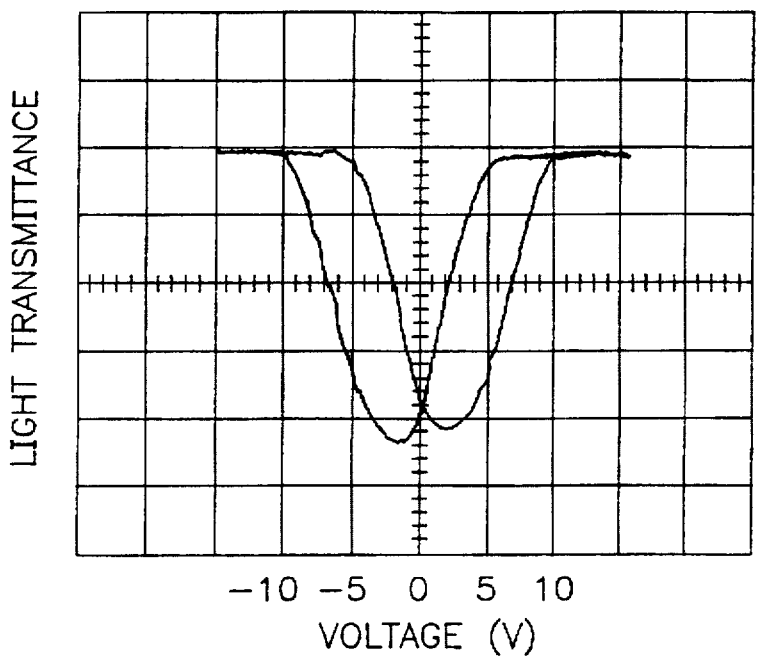
FIG. 8 shows an optical response of the compound obtained in Comparative Example 2 to triangular wave voltage at 60° C.

Further, concerning the compound of Comparative Example 2, a test cell was driven by charging a triangular wave voltage of ±20V, 1 Hz to the test cell at each temperature of 108° C., 80° C. and 60° C. to study a change in transmitted light. FIGS. 6, 7 and 8 show the results.

The texture observation at 108° C. showed a texture formed of a mixture of twist in a ferroelectric skate and a uniform state domain, while the optical response was complicated as shown in FIG. 6. The texture observation at 80° C. and 60° C. showed a twist state domain alone, and accordingly, in an optical response, the test cell showed no good dark state when the charged voltage was 0.

Example 13

Preparation of 3-fluoro-4-(1-trifluoromethyl-5-ethoxy-pentyloxycarbonyl)phenyl=4'-n-nonyloxybiphenyl-4-carboxylate (compound of the general formula (1) in which

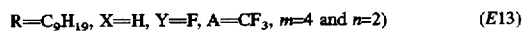
$R=C_9H_{19}$, $X=H$, $Y=F$, $A=CF_3$, $m=4$ and $n=2$)  (E13)

An end product was obtained in the same manner as in Example 1 except that R-(+)-5-ethoxy-1,1,1-trifluoro-2-pentanol was replaced with R-(+)-6-methoxy-1,1,1-trifluoro-2-hexanol.

The obtained compound was measured for physical properties in the same manner as in Example 1, and the NMR of the compound and the results are shown in Table 2 and 5.

Examples 14–19

Preparation of 3-fluoro-4-(1-trifluoromethyl-5-ethoxy-pentyloxycarboxyl)phenyl=4'-n-hexyloxybiphenyl-4-carboxylate (compound of the general formula (I) in which $R=C_6H_{13}$, $X=H$, $Y=F$, $A=CF_3$, $m=4$ and $n=2$)  (E14), 3-fluoro-4-(1-trifluoromethyl-5-ethoxy-pentyloxycarbonyl)phenyl=4'-n-heptyloxybiphenyl-4-carboxylate (compound of the general formula (1) in which $R=C_7H_{15}$, $X=H$, $Y=F$, $A=CF_3$, $m=4$ and $n=2$)  (E15)

3-fluoro-4-(1-trifluoromethyl-5-ethoxy-pentyloxycarbonyl)phenyl=4'-n-octyloxybiphenyl-4-carboxylate (compound of the general formula (1) in which $R=C_8H_{17}$, $X=H$, $Y=F$, $A=CF_3$, $m=4$ and $n=2$)  (E16), 3-fluoro-4-(1-trifluoromethyl-5-ethoxy-pentyloxycarbonyl)phenyl=4'-n-decyloxybiphenyl-4-carboxylate (compound of the general formula (1) in which

$R=C_{10}H_{23}$, $X=H$, $Y=F$, $A=CF_3$, $m=4$ and $n=2$)  (E17), 3-fluoro-4-(1-trifluoromethyl-5-ethoxy-pentyloxycarbonyl)phenyl=4'-n-undecyloxybiphenyl-4-carboxylate (compound of the general formula (1) in which $R=C_{11}H_{23}$, $X=H$, $Y=F$, $A=CF_3$, $m=4$ and $n=2$)  (E18)

and 3-fluoro-4-(1-trifluoromethyl-5-ethoxy-pentyloxycarbonyl)phenyl=4'-n-dodecyloxybiphenyl-4-carboxylate (compound of the general formula (1) in which $R=C_{12}H_{25}$, $X=H$, $Y=F$, $A=CF_3$, $m=4$ and $n=2$)  (E19)

End products were obtained in the same manner as in Example 13 except that 4-(4'-n-nonyloxy) biphenylcarboxylic acid was replaced with 4-(4'-n-hexyloxy)biphenylcarboxylic acid (Example 14), 4-(4'-n-heptyloxy)biphenylcarboxylic acid (Example 15), 4-(4'-n-octyloxy)biphenylcarboxylic acid (Example 16), 4-(4'-n-decyloxy)biphenylcarboxylic acid (Example 17), 4-(4'-n-undecyloxy)biphenylcarboxylic acid (Example 18) or 4-(4'-n-dodecyloxy)biphenylcarboxylic acid (Example 19). The NMR of the compounds and the results are shown in Tables 2 and 5.

Examples 20 and 21

Preparation of
3-fluoro-4-(1-trifluoromethyl-5-propyloxy-pentyloxycarbonyl)phenyl=4'-n-nonyloxybiphenyl-4-carboxylate (compound of the general formula (1) in which $R=C_9H_{19}$, $X=H$, $Y=F$, $A=CF_3$, $m=4$ and $n=3$)  (E20)

and 3-fluoro-4-(1-trifluoromethyl-5-butoxy-pentyloxycarbonyl)phenyl=4'-n-nonyloxybiphenyl-4-carboxylate (compound of the general formula (1) in which $R=C_9H_{19}$, $X=H$, $Y=F$, $A=CF_3$, $m=4$ and $n=4$)  (E21)

End products were obtained in the same manner as in Example 13 except that R-(+)-6-ethoxy-1,1,1-trifluoro-2-hexanol was replaced with R-(+)-6-propyloxy-1,1,1-trifluoro-2-hexanol (Example 20) or R-(+)-6-buthoxy-1,1,1-trifluoro-2-hexanol (Example 21), and the NMR of the compounds and the results are shown in Tables 2 and 5.

Example 22

Preparation of 4-(1-trifluoromethyl-5-ethoxy-pentyloxycarbonyl)phenyl=4'-n-nonyloxybiphenyl-4-carboxylate (compound of the general formula (1) in which $R=C_9H_{19}$, $X=H$, $Y=H$, $A=CF_3$, $m=4$ and $n=2$)  (E22)

An end product was obtained in the same manner as in Example 1 except that 2-fluoro-4-acetoxybenzoic acid was replaced with 4-acetoxybenzoic acid.

The obtained compound was measured for physical properties in the same manner as in Example 1, and the NMR and the compound and the results are shown Tables 2 and 5.

Examples 23–27

Preparation of
4-(1-trifluoromethyl-5-ethoxy-pentyloxycarbonyl) phenyl=4'-n-heptyloxybiphenyl-4-carboxylate (compound of the general formula (1) in which $R=C_7H_{15}$, $X=H$, $Y+H$, $A=CF_3$, $m=4$ and $n=2$)  (E23), 4-(1-trifluoromethyl-5-ethoxy-pentyloxycarbonyl)
phenyl=4'-n-octyloxybiphenyl-4-carboxylate
(compound of the general formula (1) in which R=$C_8H_{17}$, X=H, Y=H, A=$CF_3$, m=4 and n=2)  (E24), 4-(1-trifluoromethyl-5-ethoxy-pentyloxycarbonyl)
phenyl=4'-n-decyloxybiphenyl-4-carboxylate
(compound of the general formula (1) in which R=$C_{10}H_{21}$, X=H, Y=H, A=$CF_3$, m=4 and n=2)  (E25), 4-(1-trifluoromethyl-5-ethoxy-pentyloxycarbonyl)
phenyl=4'-n-undecyloxybiphenyl-4-carboxylate
(compound of the general formula (1) in which R=$C_{11}H_{23}$, X=H, Y=H, A=$CF_3$, m=4 and n=2)  (E26)

and
(1-trifluoromethyl-5-ethoxy-pentyloxycarbonyl)phenyl=
4'-n-dodecyloxybiphenyl-4-carboxylate (compound of
the general formula (1) in which R=$C_{12}H_{25}$, X=H, Y=H, A=$CF_3$, m=4 and n=2)  (E27)

End products were obtained in the same manner as in
Example 21 except that 4-(4'-n-nonyloxy)
biphenylcarboxylic acid was replaced with 4-(4'-n-
heptyloxy)biphenylcarboxylic acid (Example 23), 4-(4'-n-
octyloxy)biphenylcarboxylic acid (Example 24), 4-(4'-n-
decyloxy)biphenylcarboxylic acid (Example 25), 4-(4'-n-
undecyloxy)biphenylcarboxylic acid (Example 26) or 4-(4'-
n-dodecyloxy)biphenylcarboxylic acid (Example 27). The
NMR of the compounds and the results are shown in Tables
2 and 5.

Examples 28 and 29

Preparation of
4-(1-trifluoromethyl-5-propyloxy-pentyloxycarbonyl)
phenyl=4'-n-nonyloxybiphenyl-4-carboxylate
(compound of the general formula (1) in which R=$C_9H_{19}$, X=H, Y=H, A=$CF_3$, m=4 and n=3)  (E28)

and
4-(1-trifluoromethyl-5-butoxy-pentyloxycarbonyl)
phenyl=4'-n-nonyloxybiphenyl-4-carboxylate
(compound of the general formula (1) in which R=$C_9H_{19}$, X=H, Y=H, A=$CF_3$, m=4 and n=4)  (E29)

End products were obtained in the same manner as in
Example 21 except that R-(+)-6-ethoxy-1,1,1-trifluoro-2-
hexanol was replaced with R-(+)-6-propyloxy-1,1,1-
trifluoro-2-hexanol (Example 28) or R-(+)-6-buthoxy-1,1,1-
trifluoro-2-hexanol (Example 29), and the NMR of the
compounds and the results are shown in Tables 2 and 5.

Example 30

Preparation of 2-fluoro-4-(1-trifluoromethyl-5-ethoxy-
pentyloxycarbonyl)phenyl=4'-n-nonyloxybiphenyl-4-
carboxylate (compound of the general formula (1) in which R=$C_9H_{19}$, X=F, Y=H, A=$CF_3$, m=4 and n=2)  (E30)

An end product was obtained in the same manner as in
Example 13 except that 3-fluoro-4-hydroxybenzoic acid was replaced with 3-fluoro-4-hydroxybenzoic acid. The NMR of
the compound and the results are shown in Tables 2 and 5.

Examples 31 and 32

Preparation of
2-fluoro-4-(1-trifluoromethyl-5-ethoxy-
pentyloxycarbonyl)phenyl=4'-n-octyloxybiphenyl-4-
carboxylate (compound of the general formula (1) in
which R=$C_8H_{17}$, X=F, Y=H, A=$CF_3$, m=4 and n=2)  (E31)

and
2-fluoro-4-(1-trifluoromethyl-5-ethoxy-
pentyloxycarbonyl)phenyl=4'-n-decyloxybiphenyl-4-
carboxylate (compound of the general formula (1) in
which R=$C_{10}H_{21}$, X=F, Y=H, A=$CF_3$, m=4 and n=2)  (E32)

End products were obtained in the same manner as in
Example 30 except that 4-(4'-n-nonyloxy)
biphenylcarboxylic acid was replaced with 4-(4'-n-octyloxy)
biphenylcarboxylic acid (Example 31) or 4-(4'-n-
dodecyloxy)biphenylcarboxylic acid (Example 32. The
NMR of the compounds and the results are shown in Tables
2 and 5.

Examples 33 and 34

Preparation of
2-fluoro-4-(1-trifluoromethyl-5-propyloxy-
pentyloxycarbonyl)phenyl=4'-n-nonyloxybiphenyl-4-
carboxylate (compound of the general formula (1) in
which R=$C_9H_{19}$, X=F, Y=H, A=$CF_3$, m=4 and n=3)  (E33)

and
2-fluoro-4-(1-trifluoromethyl-5-butoxy-
pentyloxycarbonyl)phenyl=4'-n-nonyloxybiphenyl-4-
carboxylate (compound of the general formula (1) in
which R=$C_9H_{19}$, X=F, Y=H, A=$CF_3$, m=4 and n=4)  (E34)

End products were obtained in the same manner as in
Example 30 except that R-(+)-6-ethoxy-1,1,1-trifluoro-2-
hexanol was replaced with R-(+)-6-propyloxy-1,1,1-
trifluoro-2-hexanol (Example 33) or R-(+)-6-butoxy-1,1,1-
trifluoro-2-hexanol (Example 34). The NMR of the
compounds and the results are shown in Tables 2 and 5.

Comparative Example 3

Preparation of 3-fluoro-4-(1-trifluoromethyl-5-methoxy-
pentyloxycarboxyl)phenyl=4'-n-octyloxybiphenyl-4-
carboxylate (compound of the general formula (1) in which R=$C_8H_{17}$, X=H, Y=F, A=$CF_3$, m=4 and n=1)  (CE3)

An end product was obtained in the same manner as in
Example 13 except that R-(+)-6-ethoxy-1,1,1-trifluoro-2-
hexanol was replaced with R-(+)-6-methoxy-1,1,1-trifluoro-
2-hexanol. The NMR of the compound and the results are
shown in Tables 2 and 6.

Comparative Example 4

Preparation of 3-fluoro-4-(1-trifluoromethyl-5-methoxy-
pentyloxycarboxyl)phenyl=4'-n-undecyloxybiphenyl-4-
carboxylate (compound of the general formula (1) in which R=$C_{11}H_{23}$, X=H, Y=F, A=$CF_3$, m=4 and n=1)　　(CE4)

An end product was obtained in the same manner as in Example 7 except that 4-(4'-n-octyloxy)biphenylcarboxylic acid was replaced with 4-(4'-n-undecyloxy) biphenylcarboxylic acid. The NMR of the compound and the results are shown in Tables 2 and 6.

Comparative Examples 5 and 6

Preparation of 4-(1-trifluoromethyl-5-ethoxy-pentyloxycarboxyl)phenyl=4'-n-hexyloxybiphenyl-4-carboxylate (compound of the general formula (i) in which R=$C_6H_{13}$, X=H, Y=H, A=$CF_3$, m=4 and n=2)　　(CE5)

and
4-(1-trifluoromethyl-5-methoxy-pentyloxycarboxyl)phenyl=4'-n-octyloxybiphenyl-4-carboxylate (compound of the general formula (1) in which R=$C_8H_{17}$, X=H, Y=H, A=$CF_3$, m=4 and n=1)　　(CE6)

End products were obtained in the same manner as in Example 21 except that 4-(4'-n-nonyloxy) biphenylcarboxylic acid was replaced with 4-(4'-n-hexyloxy)biphenylcarboxylic acid (Comparative Example 5) or that R-(+)-6-ethoxy-1,1,1-trifluoro-2-hexanol was replaced with R-(+)-6-methoxy-1,1,1-trifluoro-2-hexanol (Comparative Example 6). The NMR of the compounds and the results are shown in Tables 2 and 6.

Comparative Example 7

Preparation of 2-fluoro-4-(1-trifluoromethyl-5-ethoxy-pentyloxycarbonyl)phenyl=4'-n-heptyloxybiphenyl-4-carboxylate (compound of the general formula (1) in which R=$C_7H_{15}$, X=F, Y=H, A=$CF_3$, m=4 and n=2)　　(CE7)

An end product was obtained in the same manner as in Example 30 except that 4-(4'-n-nonyloxy) biphenylcarboxylic acid was replaced with 4-(4'-n-heptyloxy)biphenylcarboxylic acid. The NMR of the compound and the results are shown in Tables 2 and 6.

Comparative Example 8

Preparation of 2-fluoro-4-(1-trifluoromethyl-5-methoxy-pentyloxycarbonyl)phenyl=4'-n-nonyloxybiphenyl-4-carboxylate (compound of the general formula (1) in which R=$C_9H_{19}$, X=F, Y=H, A=$CF_3$, m=4 and n=1)　　(CE8)

An end product was obtained in the same manner as in Example 30 except that R-(+)-6-ethoxy-1,1,1-trifluoro-2-hexanol was replaced with R-(+)-6-methoxy-1,1,1-trifluoro-2-hexanol. The NMR of the compound and the results are shown in Tables 2 and 6.

Example 35

Preparation of 3-fluoro-4-(1-trifluoromethyl-3-ethoxy-propyloxycarbonyl)phenyl=4'-n-octyloxybiphenyl-4-carboxylate (compound of the general formula (1) in which R=$C_8H_{17}$, X=H, Y=F, A=$CF_3$, m=2 and n=2)　　(E35)

An end product was obtained in the same manner as in Example 1 except that R-(+)-5-ethoxy-1,1,1-trifluoro-2-pentanol was replaced with R-(+)-4-ethoxy-1,1,1-trifluoro-2-butanol. The NMR of the compound and the results are shown in Tables 3 and 7.

Example 36

Preparation of 4-(1-trifluoromethyl-3-ethoxy-propyloxycarbonyl)phenyl=4'-n-nonyloxybiphenyl-4-carboxylate (compound of the general formula (1) in which R=$C_9H_{19}$, X=H, Y=H, A=$CF_3$, m=2 and n=2)　　(E36)

An end product was obtained in the same manner as in Example 35 except that 2-fluoro-4-acetoxybenzoic acid was replaced with 4-acetoxybenzoic acid. The NMR of the compound and the results are shown in Tables 3 and 7.

Example 37

Preparation of 2-fluoro-4-(1-trifluoromethyl-3-ethoxy-propyloxycarbonyl)phenyl=4'-n-nonyloxybiphenyl-4-carboxylate (compound of the general formula (1) in which R=$C_9H_{19}$, X=F, Y=H, A=$CF_3$, m=2 and n=2)　　(E37)

An end product was obtained in the same manner as in Example 35 except that 2-fluoro-4-acetoxybenzoic acid was replaced with 3-fluoro-4-acetoxybenzoic acid. The NMR of the compound and the results are shown in Tables 3 and 7.

Example 38

Preparation of 3-fluoro-4-(1-pentafluoroethyl-5-ethoxy-pentyloxycarbonyl)phenyl=4'-n-octyloxybiphenyl-4-carboxylate (compound of the general formula (1) in which R=$C_8H_{17}$, X=H, Y=F, A=$C_2F_5$, m=4 and n=2)　　(E38)

An end product was obtained in the same manner as in Example 1 except that R-(+)-5-ethoxy-1,1,1-trifluoro-2-pentanol was replaced with R-(+)-5-ethoxy-1,1,1-trifluoro-2,2-difluoro-3-pentanol. The NMR of the compound and the results are shown in Tables 3 and 7.

Examples 39 and 40

Preparation of
3-fluoro-4-(1-pentafluoroethyl-5-ethoxy-pentyloxycarbonyl)phenyl=4'-n-decyloxybiphenyl-4-carboxylate (compound of the general formula (1) in which R=$C_{10}H_{21}$, X=H, Y=F, A=$C_2F_5$, m=4 and n=2)　　(E39)

and
3-fluoro-4-(1-pentafluoroethyl-5-ethoxy-pentyloxycarbonyl)phenyl=4'-n-undecyloxybiphenyl-4-carboxylate (compound of the general formula (1) in which R=$C_{11}H_{23}$, X=H, Y=F, A=$C_2F_5$, m=4 and n=2)　　(E40)

End products were obtained in the same manner as in Example 38 except that 4-(4'-octyloxy)biphenylcarboxylic acid was replaced with 4-(4'-decyloxy)biphenylcarboxylic acid (Example 39) or 4-(4'-n-undecyloxy) biphenylcarboxylic acid (Example 40). The NMR of the compounds and the results are shown in Tables 3 and 7.

As described above, the 1H-NMR spectrum data and the results of each compounds are shown in Tables 1 to 7 and the physical properties are shown in Tables 8 to 11, which are given below. In Tables 4 to 11, the abbreviations stand for as follows.

Cr=crystal phase, SA=smectic A phase, SC*=smectic C phase (ferroelectric phase), SCγ*=Chiral smectic Cγ phase (ferrielectric phase), SCA*=chiral smectic A phase (antiferroelectric phase), SX=unidentified phase (which exhibited an optical response similar to that of an antiferroelectric phase and is assumed to be similar to SCα* phase found in MHPOBC), I=isotropic phase, and Parenthesized values=phase transition temperatures (°C.)

TABLE 1

| Compound No. | Hydrogen atom number | | | | | | |
|---|---|---|---|---|---|---|---|
| | 1 | 2 | 3, 4 | 5 | 6 | 7 | 8 |
| E1–E6 | 4.0 | 7.0 | 7.6–7.7 | 8.2 | 7.2 | 8.1 | 5.6 |
| E7–E9 | 4.0 | 7.0 | 7.6–7.7 | 8.2 | 7.3 | 8.2 | 5.6 |
| E10–E12 | 4.0 | 7.0 | 7.6–7.7 | 8.2 | 7.4 | 7.9 | 5.6 |
| CE1, CE2 | 4.0 | 7.0 | 7.6–7.7 | 8.2 | 7.2 | 8.1 | 5.6 |

TABLE 2

| Compound No. | Hydrogen atom number | | | | | | |
|---|---|---|---|---|---|---|---|
| | 1 | 2 | 3, 4 | 5 | 6 | 7 | 8 |
| E13–E21 | 4.0 | 7.0 | 7.6–7.7 | 8.2 | 7.2 | 8.1 | 5.6 |
| E22–E29 | 4.0 | 7.0 | 7.6–7.7 | 8.2 | 7.3 | 8.2 | 5.6 |
| E30–E34 | 4.0 | 7.0 | 7.6–7.7 | 8.2 | 7.9 | 7.4 | 5.6 |
| CE3, CE4 | 4.0 | 7.0 | 7.6–7.7 | 8.2 | 7.2 | 8.1 | 5.6 |
| CE5, CE6 | 4.0 | 7.0 | 7.6–7.7 | 8.2 | 7.4 | 8.2 | 5.6 |

TABLE 2-continued

| Compound No. | Hydrogen atom number | | | | | | |
|---|---|---|---|---|---|---|---|
| | 1 | 2 | 3, 4 | 5 | 6 | 7 | 8 |
| CE7, CE8 | 4.0 | 7.0 | 7.6–7.7 | 8.2 | 7.9 | 7.4 | 5.6 |

TABLE 3

| Compound No. | Hydrogen atom number | | | | | | |
|---|---|---|---|---|---|---|---|
| | 1 | 2 | 3, 4 | 5 | 6 | 7 | 8 |
| E35 | 4.0 | 7.0 | 7.6–7.7 | 8.2 | 7.2 | 8.1 | 5.6 |
| E36 | 4.0 | 7.0 | 7.6–7.7 | 8.2 | 7.4 | 8.2 | 5.6 |
| E37 | 4.0 | 7.0 | 7.6–7.7 | 8.2 | 7.4 | 8.0 | 5.6 |
| E38, E39 | 4.0 | 7.0 | 7.6–7.7 | 8.2 | 7.2 | 8.1 | 5.8 |
| E40 | 4.0 | 7.0 | 7.6–7.7 | 8.2 | 7.2 | 8.0 | 5.6 |

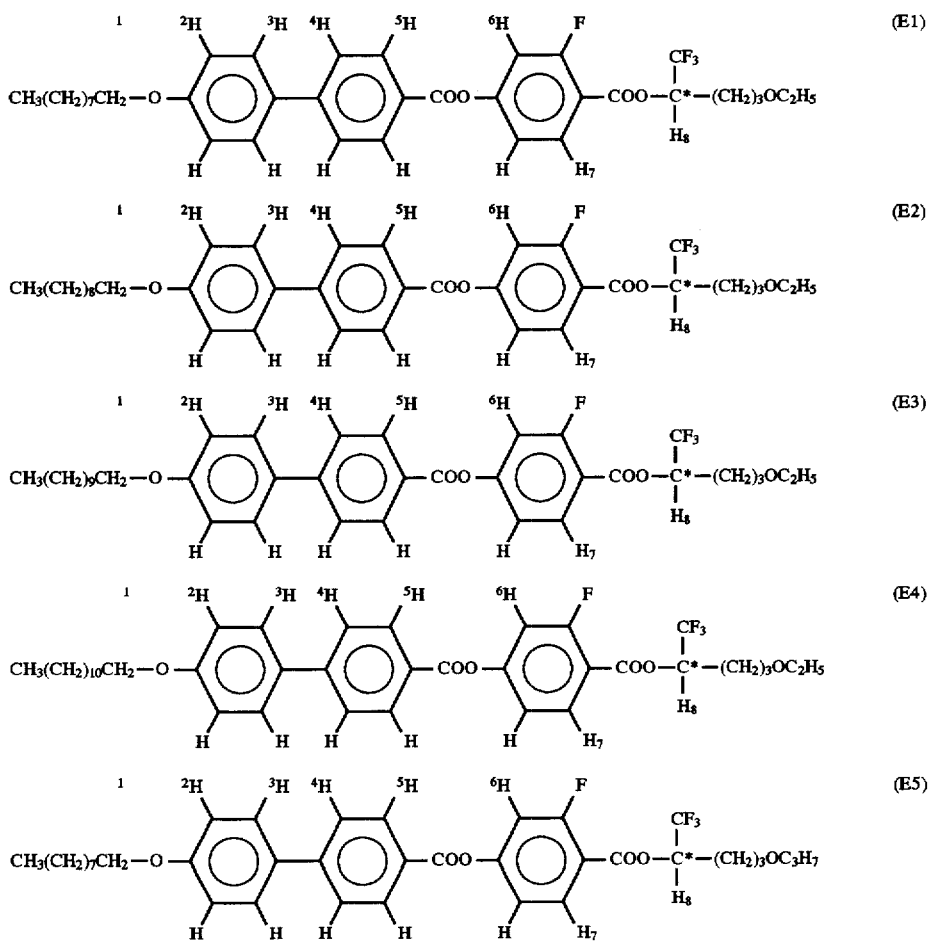

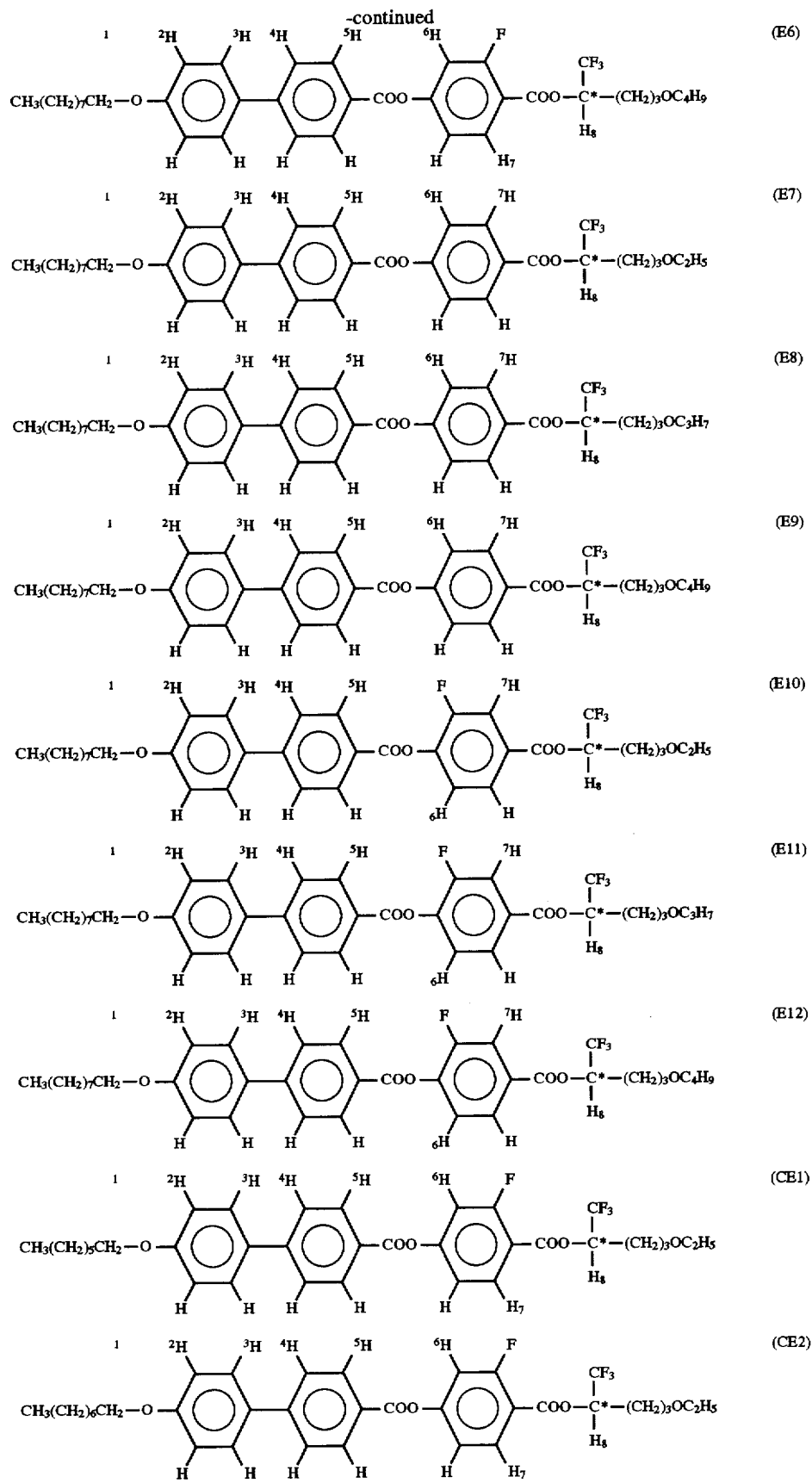

-continued
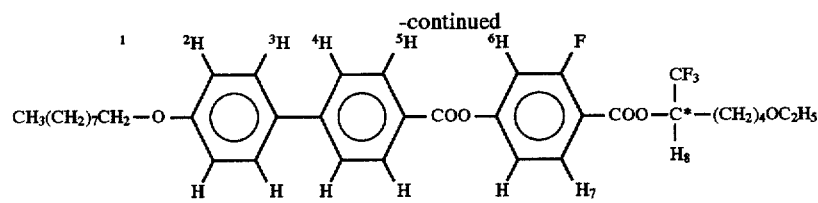
(E13)
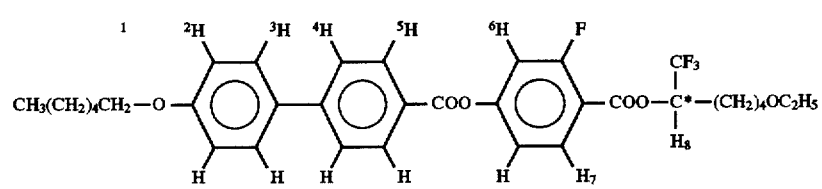
(E14)
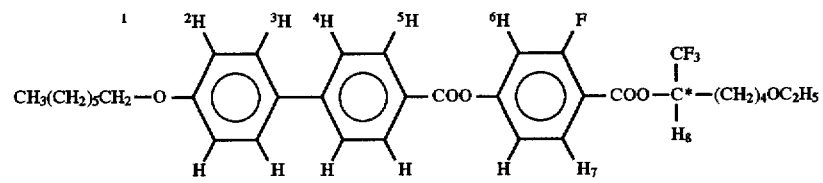
(E15)
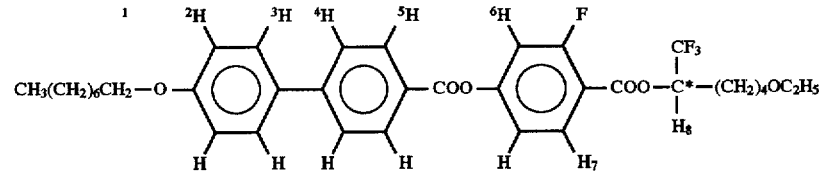
(E16)
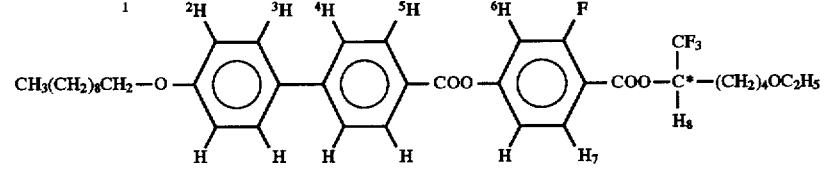
(E17)
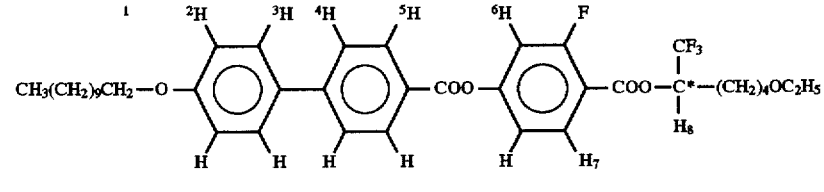
(E18)
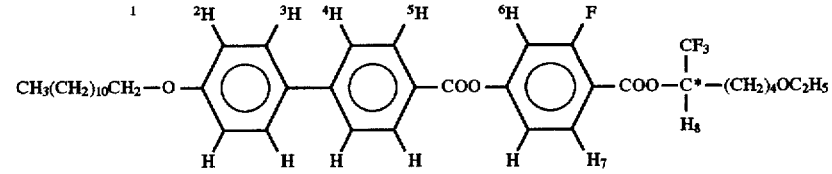
(E19)
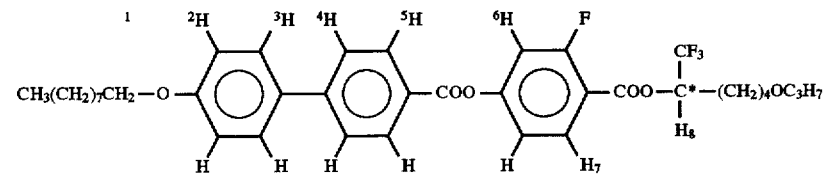
(E20)
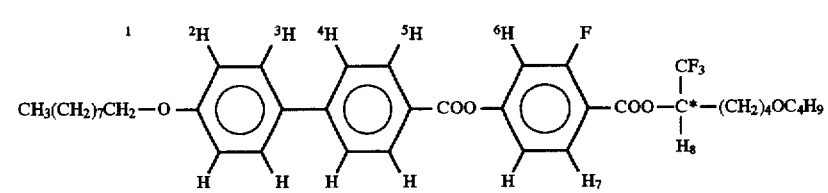
(E21)

-continued
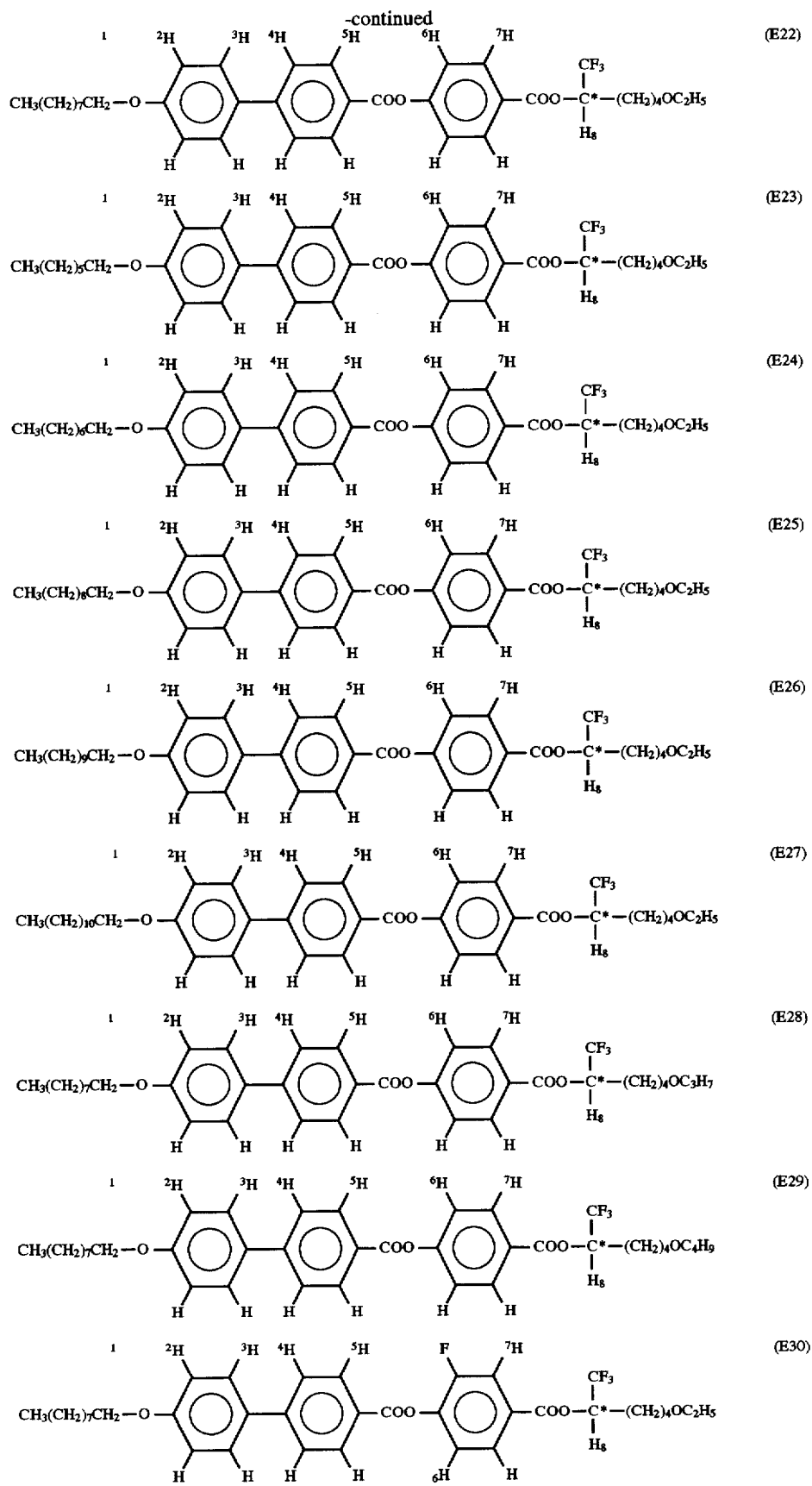

-continued
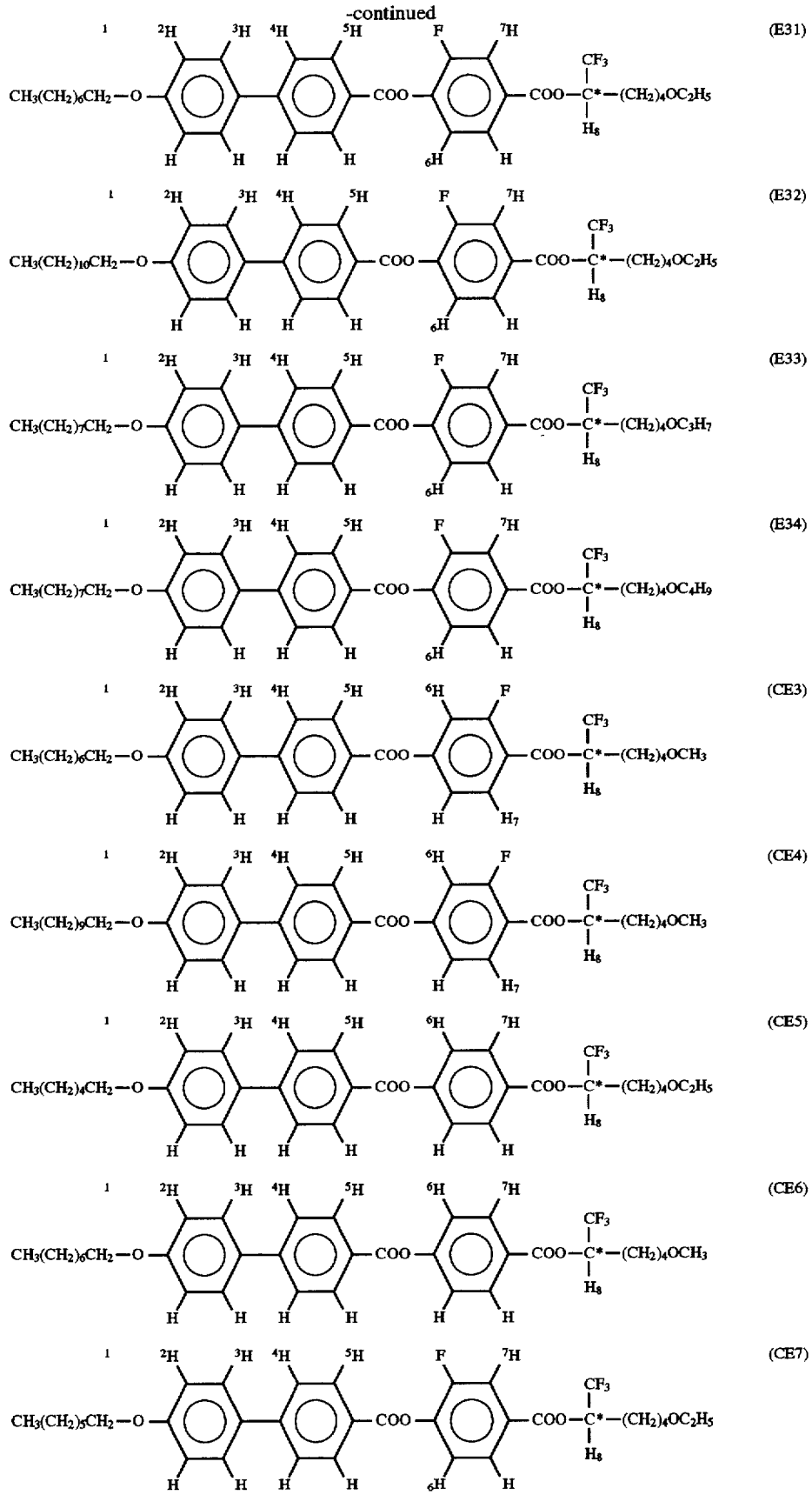

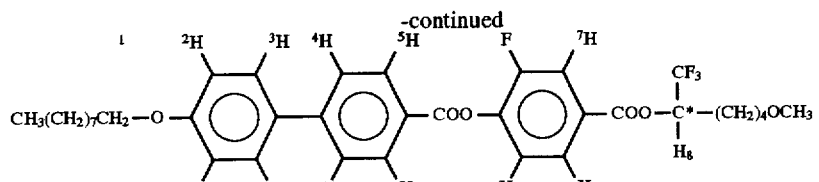
(CE8)

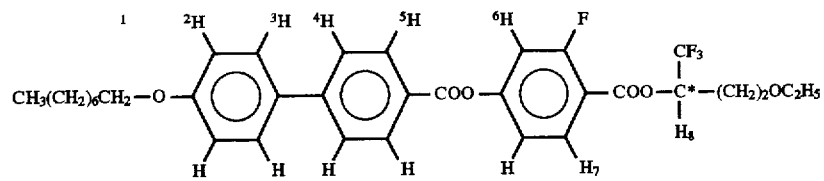
(E35)

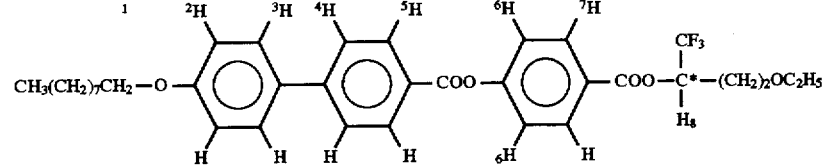
(E36)

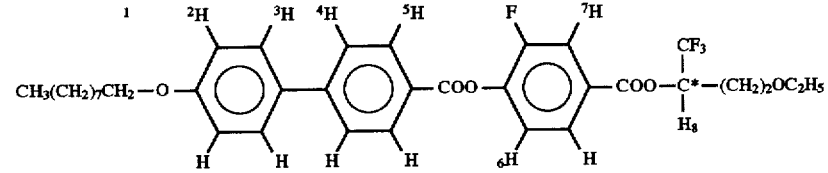
(E37)

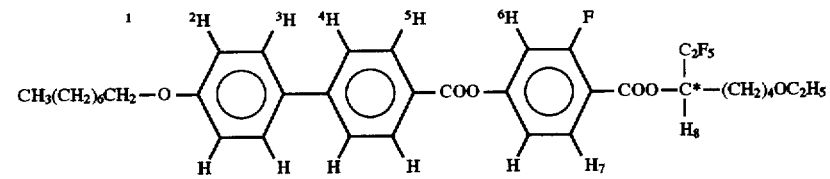
(E38)

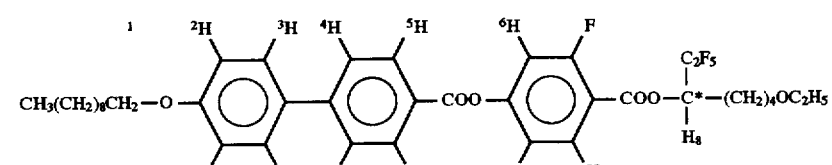
(E39)

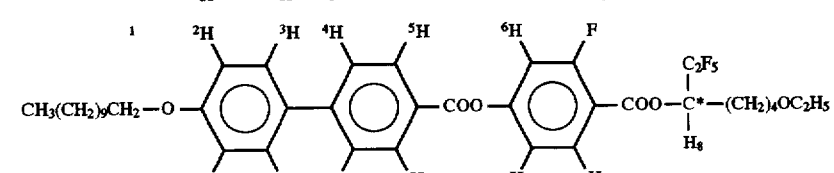
(E40)

TABLE 4

| | Phase sequence | | | | | | |
|---|---|---|---|---|---|---|---|
| Example 1 (E1) | Cr | (34) | SCγ* | (101) | SA | (103) | I |
| Example 2 (E2) | Cr | (33) | SCγ* | (98) | SA | (99) | I |
| Example 3 (E3) | Cr | (35) | SCγ* | (95) | SA | (96) | I |
| Example 4 (E4) | Cr | (41) | SCγ* | (92) | SA | (94) | I |
| Example 5 (E5) | Cr | (<−10) | SCγ* | (99) | SA | (102) | I |
| Example 6 (E6) | Cr | (<−10) | SCγ* | (92) | SA | (95) | I |
| Example 7 (E7) | Cr | (61) | SCγ* | (108) | SA | (115) | I |
| Example 8 (E8) | Cr | (56) | SCγ* | (104) | SA | (110) | I |
| Example 9 (E9) | Cr | (50) | SCγ* | (97) | SA | (105) | I |
| Example 10 (E10) | Cr | (71) | SCγ* | (81) | SA | (99) | I |
| Example 11 (E11) | Cr | (66) | SCγ* | (76) | SA | (94) | I |
| Example 12 (E12) | Cr | (60) | SCγ* | (69) | SA | (89) | I |

TABLE 4-continued

| | Phase sequence | | | | | | |
|---|---|---|---|---|---|---|---|
| Comp. Ex. 1 (CE1) | Cr | (62) | SC* | (113) | SA | (116) | I |
| Comp. Ex. 2 (CE2) | Cr | (56) | SC* | (108) | SX | (110) | I |

TABLE 5

| | Phase sequence | | | | | | |
|---|---|---|---|---|---|---|---|
| Example 13 (E13) | Cr | (<−10) | SCγ* | (89) | SA | (91) | I |
| Example 14 (E14) | Cr | (46) | SCγ* | (107) | SA | (115) | I |

TABLE 5-continued

| | | Phase sequence | | | | | |
|---|---|---|---|---|---|---|---|
| Example 15 (E15) | Cr | (51) | SCγ* | (98) | SX | (103) | I |
| Example 16 (E16) | Cr | (46) | SCγ* | (95) | SA | (98) | I |
| Example 17 (E17) | Cr | (<-10) | SCγ* | (85) | SX | (86) | I |
| Example 18 (E18) | Cr | (29) | SCγ* | (82) | SX | (84) | I |
| Example 19 (E19) | Cr | (40) | SCγ* | (82) | SX | (83) | I |
| Example 20 (E20) | Cr | (<-10) | SCγ* | (84) | SX | (88) | I |
| Example 21 (E21) | Cr | (<-10) | SCγ* | (79) | SX | (84) | I |
| Example 22 (E22) | Cr | (41) | SCγ* | (95) | SA | (103) | I |
| Example 23 (E23) | Cr | (93) | SCγ* | (104) | SX | (118) | I |
| Example 24 (E24) | Cr | (57) | SCγ* | (101) | SA | (111) | I |
| Example 25 (E25) | Cr | (48) | SCγ* | (92) | SA | (99) | I |
| Example 26 (E26) | Cr | (28) | SCγ* | (86) | SX | (93) | I |
| Example 27 (E27) | Cr | (54) | SCγ* | (85) | SX | (90) | I |
| Example 28 (E28) | Cr | (41) | SCγ* | (88) | SA | (96) | I |
| Example 29 (E29) | Cr | (37) | SCγ* | (83) | SA | (95) | I |
| Example 30 (E30) | Cr | (47) | SCγ* | (66) | SA | (85) | I |
| Example 31 (E31) | Cr | (62) | SCγ* | (73) | SA | (97) | I |
| Example 32 (E32) | Cr | (40) | SCγ* | (61) | SA | (73) | I |
| Example 33 (E33) | Cr | (41) | SCγ* | (60) | SA | (82) | I |
| Example 34 (E34) | Cr | (40) | SCγ* | (55) | SA | (77) | I |

TABLE 6

| | Phase sequence |
|---|---|
| Comp. Ex. 3 (CE3) | Cr (38) SCA* (96) SC* (97) SA (98) I |
| Comp. Ex. 4 (CE4) | Cr (25) SCA* (79) SCγ* (83) I |
| Comp. Ex. 5 (CE5) | Cr (98) SCA* (104) SA (117) I |
| Comp. Ex. 6 (CE6) | Cr (73) SCA* (106) SA (114) I |
| Comp. Ex. 7 (CE7) | Cr (84) SA (103) I |
| Comp. Ex. 8 (CE8) | Cr (55) SCA* (71) SA (89) I |

TABLE 7

| | Phase sequence |
|---|---|
| Example 35 (E35) | Cr (58) SCγ* (104) SA (108) I |
| Example 36 (E36) | Cr (73) SCγ* (104) SA (115) I |
| Example 37 (E37) | Cr (50) SCγ* (73) SA (98) I |
| Example 38 (E38) | Cr (30) SCγ* (70) I |
| Example 39 (E39) | Cr (20) SCγ* (57) I |
| Example 40 (E40) | Cr (34) SCγ* (51) I |

Example 41

The ferrielectric liquid crystal (E16, to be referred to as 1A hereinafter) obtained in Example 15 was mixed with 20 mol % of an optically active compound (2A) of the following chemical formula, to prepare a ferrielectric liquid crystal composition.

A: $C_8H_{17}$—Ph—Ph—COO—Ph(3F)—COO—C*H($CF_3$)($CH_2$)$_4$O$C_2H_5$

A: $C_9H_{19}$—COO—Ph(2F)—COO—Ph—COO—C*H($CH_3$)$C_3H_7$

Ph=1,4-phenylene, Ph(3F) of 1A=1,4-phenylene in which F is substituted on 3-position (Y), Ph(2F) of 2A=1,4-phenylene in which F is substituted on 2-position ($X^2$), C*=asymmetric carbon The above-prepared liquid crystal composition was identified for phases and studied for an optical response. Tables 8 to 11 show the results.

The phase identification was carried out in the same manner as in Example 1. A cell for measuring the optical response was prepared in the same manner as in Example 1.

In the optical response measurement, the test cell was cooled to 30° C. and driven by charging a triangular wave voltage of ±10V, 50 mHz to the test cell to study a change in transmitted light.

The threshold voltage was measured in the test cell. When the minimum intensity of the transmitted light was taken as 0% and the maximum intensity of the transmitted light was taken as 100% the voltage at which the transmitted light intensity became 90% by phase transition from a ferrielectric phase to a ferroelectric phase was defined as threshold voltage I, and the voltage at which the threshold voltage decreased to 90% by phase transition from a ferroelectric phase to a ferrielectric phase was defined as threshold voltage II.

Further, a response time was measured in the test cell. The time required for the changing of transmitted light intensity by 90% under the application of a 8 V pulse voltage having a frequency of 10 Hz was defined as a response time.

Examples 42 and 43

The ferrielectric liquid crystal (E13, to be referred to as 1B hereinafter) obtained in Example 13 was mixed with 20 mol % of the following optically active compound (2B) or with 25 mol % of the following optically active compound (2C), to prepare ferrielectric liquid crystal compositions. The prepared ferrielectric liquid crystal compositions were measured for physical properties in the same manner as in Example 41. Tables 8 to 11 show the results.

1B; $C_9H_{19}$—O—Ph—Ph—COO—Ph(3F)—COO—C*H($CF_3$)($CH_2$)$_4$O$C_2H_5$

2B; $C_{10}H_{21}$—COO—Ph(2F)—COO—Ph—COO—C*H($CH_3$)$C_4H_9$

2C; $C_{10}H_{21}$—COO—Ph(2F)—COO—Ph—COO—C*H($CH_3$)$C_5H_{11}$

Examples 44 and 45

The ferrielectric liquid crystal (1A) was mixed with 20 mol % of the following optically active compound (2D) (Example 44) or the ferrielectric liquid crystal (1B) was mixed with 20 mol % of the following optically active compound (2E) (Example 45), to prepare ferrielectric liquid crystal compositions. The prepared ferrielectric liquid crystal compositions were measured for physical properties in the same manner as in Example 41. Tables 8 to 11 show the results.

2D ; $C_9H_9$—COO—Ph(2F)—COO—Ph—COO—C*H($CH_3$)$C_6H_{13}$

2E ; $C_9H_{19}$—COO—Ph—COO—Ph(3F)—COO—C*H($CH_3$)$C_7H_{15}$

Ph(2F)=1,4-phenylene in which fluorine is substituted on the 2-position ($X^2$), Ph(3F)=1,4-phenylene in which fluorine is substituted on the 3-position ($Y^2$).

Examples 46 and 47

The ferrielectric liquid crystal (E1, to be referred to as 1C hereinafter) obtained in Example 1 was mixed with 20 mol % of the following optically active compound (2F or 2G) to prepare ferrielectric liquid crystal compositions. The prepared ferrielectric liquid crystal compositions were measured for physical properties in the same manner as in Example 41. Tables 8 to 11 show the results.

1C; $C_9H_{19}$—O—Ph—Ph—COO—Ph(3F)—COO—C*H($CF_3$)($CH_2$)$_3$O$C_2H_5$

2F; $C_5H_{11}$—COO—Ph—COO—Ph(2F)—COO—C*H($CH_3$)$C_5H_{11}$

2G; $C_7H_{15}$—COO—Ph(2F)—COO—Ph—COO—C*H($CH_3$)$C_5H_{11}$

Examples 48–50

The ferrielectric liquid crystal (1B) was mixed with 20 mol % of the following optically active compound (2H, 2I or 2J) to prepare ferrielectric liquid crystal compositions.

The prepared ferrielectric liquid crystal compositions were measured for physical properties in the same manner as in Example 41. Tables 8 to 11 show the results.

2H; C$_9$H$_{19}$—COO—Ph—COO—Ph—COO—C*H(CH$_3$)C$_6$H$_{13}$

2I; C$_{10}$H$_{21}$—COO—Ph—COO—Ph(2F)—COO—C*H(CH$_3$)C$_8$H$_{17}$

2J; C$_{10}$H$_{21}$—COO—Ph(3F)—COO—Ph—COO—C*H(CH$_3$)C$_8$H$_{17}$

Examples 51–54

The ferrielectric liquid crystal (1C) was mixed with 20 mol % of the following optically active compound (2K, 2L, 2M or 2N) to prepare ferrielectric liquid crystal compositions.

The prepared ferrielectric liquid crystal compositions were measured for physical properties in the same manner as in Example 41. Tables 8 to 11 show the results.

2K; C$_{10}$H$_{21}$—COO—Ph(3F)—COO—Ph(3F)—COO—C*H(CH$_3$)C$_8$H$_{17}$

2L; C$_{10}$H$_{21}$—COO—Ph(3F)—COO—Ph(2F)—COO—C*H(CH$_3$)C$_8$H$_{17}$

2M; C$_{10}$H$_{21}$—COO—Ph(2F)—COO—Ph(3F)—COO—C*H(CH$_3$)C$_8$H$_{17}$

2N; C$_{10}$H$_{21}$—COO—Ph(2F)—COO—Ph(2F)—COO—C*H(CH$_3$)C$_8$H$_{17}$

Example 55

The ferrielectric liquid crystal (1B) was mixed with 40 mol % of the above optically active compound (2A) to prepare a ferrielectric liquid crystal composition.

The prepared ferrielectric liquid crystal composition was measured for physical properties in the same manner as in Example 41. Tables 8 to 11 show the results.

Examples 56–63 and Comparative Example 9

The ferrielectric liquid crystal (1B) was mixed with 25 mol % of each of the following phenyl ester compounds (2P, 2Q, 2R, 2S, 2T or 2U), 15 mol % of The following phenyl ester compound (2P) or 30 mol % of the following optically active compound (2V), to prepare ferrielectric liquid crystal compositions. And, the ferrielectric liquid crystal (1A) was mixed with 20 mol % of the following optically active compound (2W), to prepare ferrielectric liquid crystal compositions.

The prepared ferrielectric liquid crystal compositions were measured for physical properties in the same manner as in Example 41. Tables 8 to 11 show the results.

2P; C$_9$H$_{19}$—COO—Ph—COO—Ph(3F)—COO—C$_3$H$_7$

2Q; C$_9$H$_{19}$—COO—Ph—COO—Ph(3F)—COO—C$_5$H$_{11}$

2R; C$_9$H$_{19}$—COO—Ph—COO—Ph(3F)—COO—C$_7$H$_{15}$

2S; C$_9$H$_{19}$—COO—Ph—COO—Ph(3F)—COO—C$_8$H$_{17}$

2T; C$_9$H$_{19}$—COO—Ph—COO—Ph(3F)—COO—C$_{11}$H$_{23}$

2U; C$_9$H$_{19}$—COO—Ph—COO—Ph—COO—C$_7$H$_{15}$

2V; C$_{10}$H$_{21}$—COO—Ph—COO—Ph(3F)—COO—C*H(CH3)C$_7$H$_{15}$

2W; C$_9$H$_{19}$—COO—Ph—COO—Ph(3F)—COO—C*H(CF$_3$)(CH$_2$)$_5$OC$_2$H$_5$

Further, the ferrielectric liquid crystal composition of Example 63 and the ferrielectric liquid crystal (E13=1B) were measured for their light transmittance at the time when voltage was not applied. At this time, the light transmittance at the time when only a polarizer was provided was taken as 0%, while the light transmittance at the time when the phase was changed to a ferroelectric state was taken as 100%. A liquid crystal cell of which alignment film was coated on both surfaces of the substrate and rubbed was used as the test cell.

The results show that the light transmittance of the liquid crystal composition of Example 63 was 0.9% and that of the liquid crystal 1B was 3.6%, and it can be seen from the results that considerable effects were attained on the response speed and improvement of alignment.

TABLE 8

| | Phase sequence | Component | Molar ratio |
|---|---|---|---|
| Example 41 | Cr(<-20)SCγ*(75)SA(86)I | 1A/2A = | 80/20 |
| Example 42 | Cr(<-20)SCγ*(66)SA(77)I | 1B/2B = | 80/20 |
| Example 43 | Cr(<-20)SCγ*(62)SA(73)I | 1B/2C = | 75/25 |
| Example 44 | Cr(<-20)SCγ*(69)SA(75)I | 1A/2D = | 80/20 |
| Example 45 | Cr(<-20)SCγ*(67)SA(74)I | 1B/2E = | 80/20 |
| Example 46 | Cr(<-20)SCγ*(82)SA(92)I | 1C/2F = | 80/20 |
| Example 47 | Cr(<-20)SCγ*(79)SA(89)I | 1C/2G = | 80/20 |
| Example 48 | Cr(<-20)SCγ*(70)SA(78)I | 1B/2H = | 80/20 |
| Example 49 | Cr(<-20)SCγ*(62)SA(72)I | 1B/2I = | 80/20 |
| Example 50 | Cr(<-20)SCγ*(60)SA(70)I | 1B/2J = | 80/20 |
| Example 51 | Cr(<-20)SCγ*(71)SA(81)I | 1C/2K = | 80/20 |
| Example 52 | Cr(<-20)SCγ*(79)SA(83)I | 1C/2L = | 80/20 |
| Example 53 | Cr(<-20)SCγ*(74)SA(84)I | 1C/2M = | 80/20 |
| Example 54 | Cr(<-20)SCγ*(72)SA(85)I | 1C/2N = | 80/20 |
| Example 55 | Cr(<-20)SCγ*(51)SA(69)I | 1B/2A = | 60/40 |
| Example 56 | Cr(<-20)SCγ*(79)SA(98)I | 1B/2P = | 75/25 |
| Example 57 | Cr(<-20)SCγ*(78)SA(92)I | 1B/2Q = | 75/25 |
| Example 58 | Cr(<-20)SCγ*(81)SA(91)I | 1B/2R = | 75/25 |
| Example 59 | Cr(<-20)SCγ*(76)SA(87)I | 1B/2S = | 75/25 |
| Example 60 | Cr(<-20)SCγ*(74)SA(85)I | 1B/2T = | 75/25 |
| Example 61 | Cr(<-20)SCγ*(84)SA(93)I | 1B/2U = | 75/25 |
| Example 62 | Cr(<-20)SCγ*(83)SA(95)I | 1B/2P = | 85/15 |
| Example 63 | Cr(<-20)SCγ*(73)SA(82)I | 1B/2V = | 70/30 |
| Comp. Ex. 9 | Cr(<-20)SCγ*(86)SA(93)I | 1A/2W = | 80/20 |

TABLE 9

| | Phase sequence |
|---|---|
| Liquid Crystal 1A | Cr (46) SCγ* (95) SA (98) I |
| Liquid Crystal 1B | Cr(<-10)SCγ* (89) SA (91) I |
| Liquid Crystal 1C | Cr (34) SCγ* (101) SA (103) I |
| 2A | Cr(-12)SA(27)I |
| 2B | Cr (5)SA(22)I |
| 2C | Cr (0)SA(21)I |
| 2D | Cr(-7)SA(5) I |
| 2E | Cr(12) SC* (22) SA (26) I |
| 2F | Cr (1)SA(16)I |
| 2P | Cr(57)SA(77)I |
| 2Q | Cr(61)SA(72)I |
| 2R | Cr(66)SA(70)I |
| 2S | Cr(60)SA(70)I |
| 2T | Cr(40)SA(70)I |
| 2U | Cr(29)SA(69)I |
| 2V | Cr(16)SC*(23) SCγ*(26)SA(28)I |
| 2W | Cr(30)SCA*(79)SC*(83)SA(92) I |

2G–2N in the general formula (2) had no liquid crystal phase. The melting point (solidification point) of these compounds are 2G (33), 2H (27), 2I (20), 2J (23), 2K (33), 2L (21), 2M (20) and 2N (33) respectively. The parenthesized values are temperatures (°C.).

TABLE 10

| | Threshold Voltage I | Threshold Voltage II | Response time (μ sec.) | Temperature (°C.) | Component | Molar ratio |
|---|---|---|---|---|---|---|
| Example 41 | 2.6 | 2.0 | 88 | 30 | 1A/2A = | 80/20 |
| Example 42 | 1.2 | 1.2 | 58 | " | 1B/2B = | 80/20 |
| Example 43 | 1.4 | 1.4 | 77 | " | 1B/2C = | 75/25 |
| Example 44 | 1.6 | 1.6 | 58 | " | 1A/2D = | 80/20 |
| Example 45 | 1.4 | 1.4 | 65 | " | 1B/2E = | 80/20 |
| Example 46 | 2.2 | 2.2 | 72 | " | 1C/2F = | 80/20 |
| Example 47 | 2.0 | 2.0 | 65 | " | 1C/2G = | 80/20 |
| Example 48 | 1.9 | 1.8 | 86 | " | 1B/2H = | 80/20 |
| Example 49 | 1.2 | 1.2 | 69 | " | 1B/2I = | 80/20 |
| Example 50 | 1.1 | 1.0 | 84 | " | 1B/2J = | 80/20 |
| Example 51 | 1.3 | 1.3 | 68 | " | 1C/2K = | 80/20 |
| Example 52 | 1.8 | 1.8 | 76 | " | 1C/2L = | 80/20 |
| Example 53 | 2.0 | 2.0 | 70 | " | 1C/2M = | 80/20 |
| Example 54 | 1.8 | 1.8 | 79 | " | 1C/2N = | 80/20 |
| Example 55 | 1.5 | 1.2 | 79 | " | 1B/2A = | 60/40 |
| Example 56 | 1.3 | 1.3 | 68 | " | 1B/2P = | 75/25 |
| Example 57 | 1.4 | 1.3 | 68 | " | 1B/2Q = | 75/25 |
| Example 58 | 1.3 | 1.3 | 65 | " | 1B/2R = | 75/25 |
| Example 59 | 1.2 | 1.1 | 63 | " | 1B/2S = | 75/25 |
| Example 60 | 1.0 | 1.0 | 59 | " | 1B/2T = | 75/25 |
| Example 61 | 1.1 | 1.1 | 65 | " | 1B/2U = | 75/25 |
| Example 62 | 1.3 | 1.3 | 64 | " | 1B/2P = | 85/15 |
| Example 63 | 2.0 | 2.0 | 73 | " | 1B/2V = | 70/30 |
| Comp. Ex. 9 | 2.0 | 1.8 | 133 | " | 1A/2W = | 80/20 |

Threshold Voltage: Unit V/μm

TABLE 11

| | | Threshold Voltage I | Threshold Voltage II | Response time (μ sec.) | Temperature (°C.) |
|---|---|---|---|---|---|
| Liquid Crystal | 1A | 2.0 | 2.0 | 118 | 30 |
| | 1B | 1.5 | 1.4 | 88 | " |
| | 1C | 2.2 | 2.2 | 100 | " |

Threshold Voltage: Unit V/μm

It can be understood clearly from Tables 8 to 11 clear that a composition which has a practical ferrielectric phase temperature range and shows an improved response time by mixing the liquid crystal compound having a ferrielectric phase in its phase sequence, provided by the present invention, and one of phenyl ester compounds (2A~2V).

What is claimed is:

1. A liquid crystal compound having a ferrielectric phase selected from the group consisting of

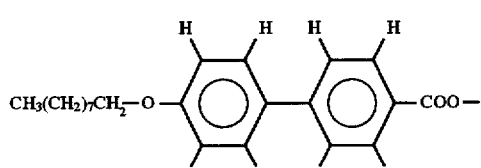

(E1)

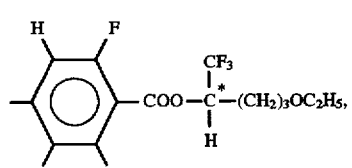

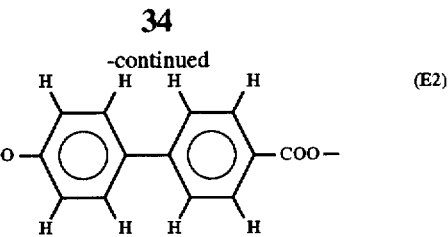

(E2)

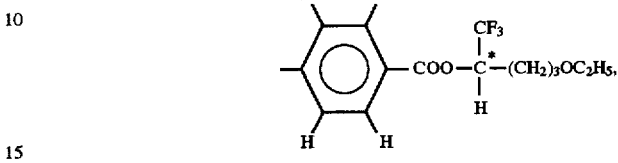

(E3)

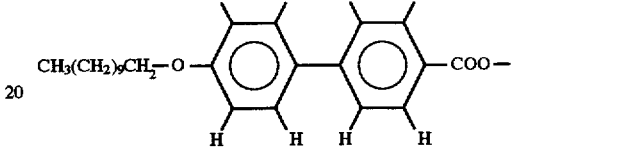

(E4)

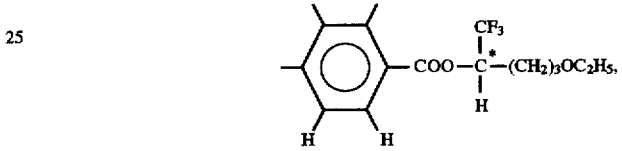

(E5)

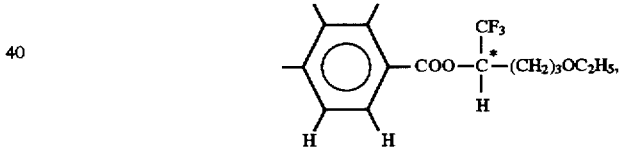

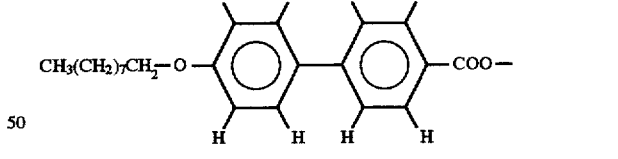

(E6)

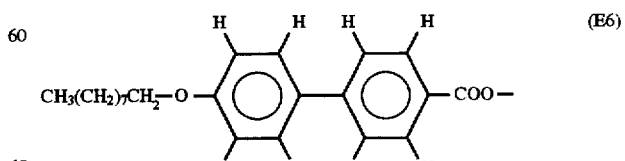

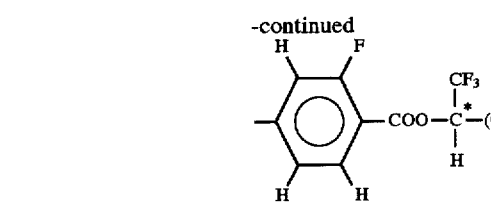
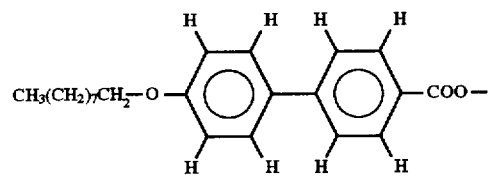
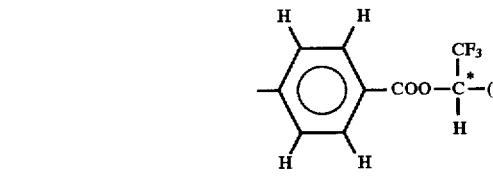
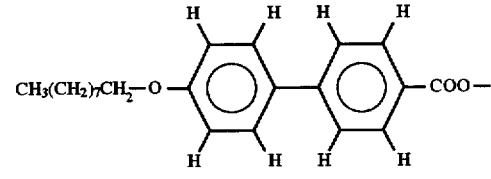
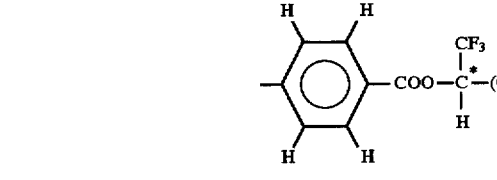
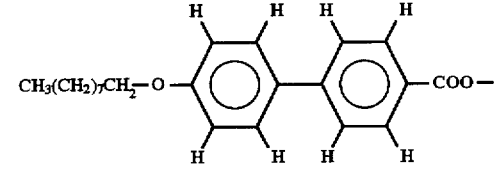
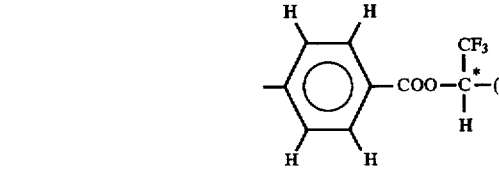
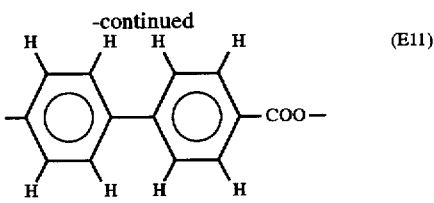
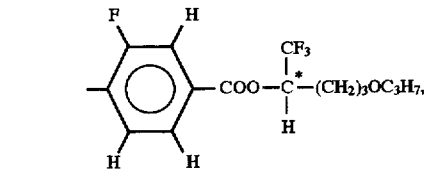
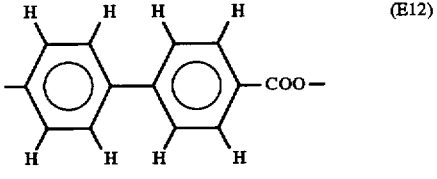
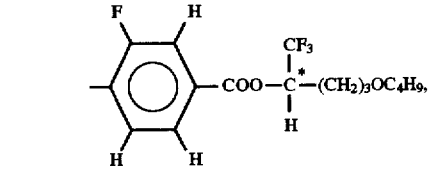
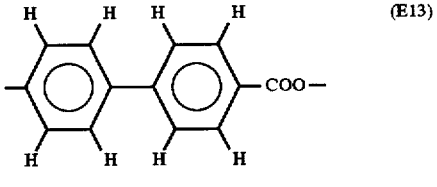
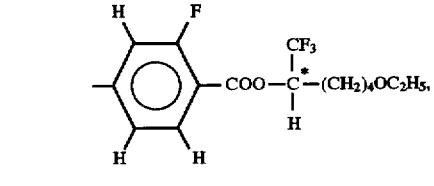
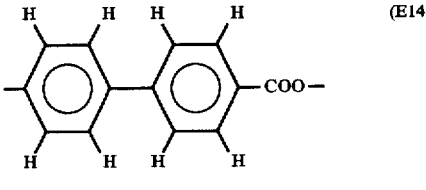
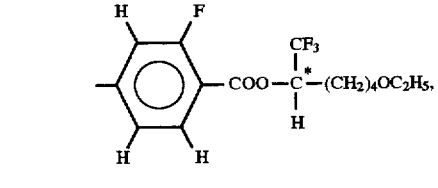

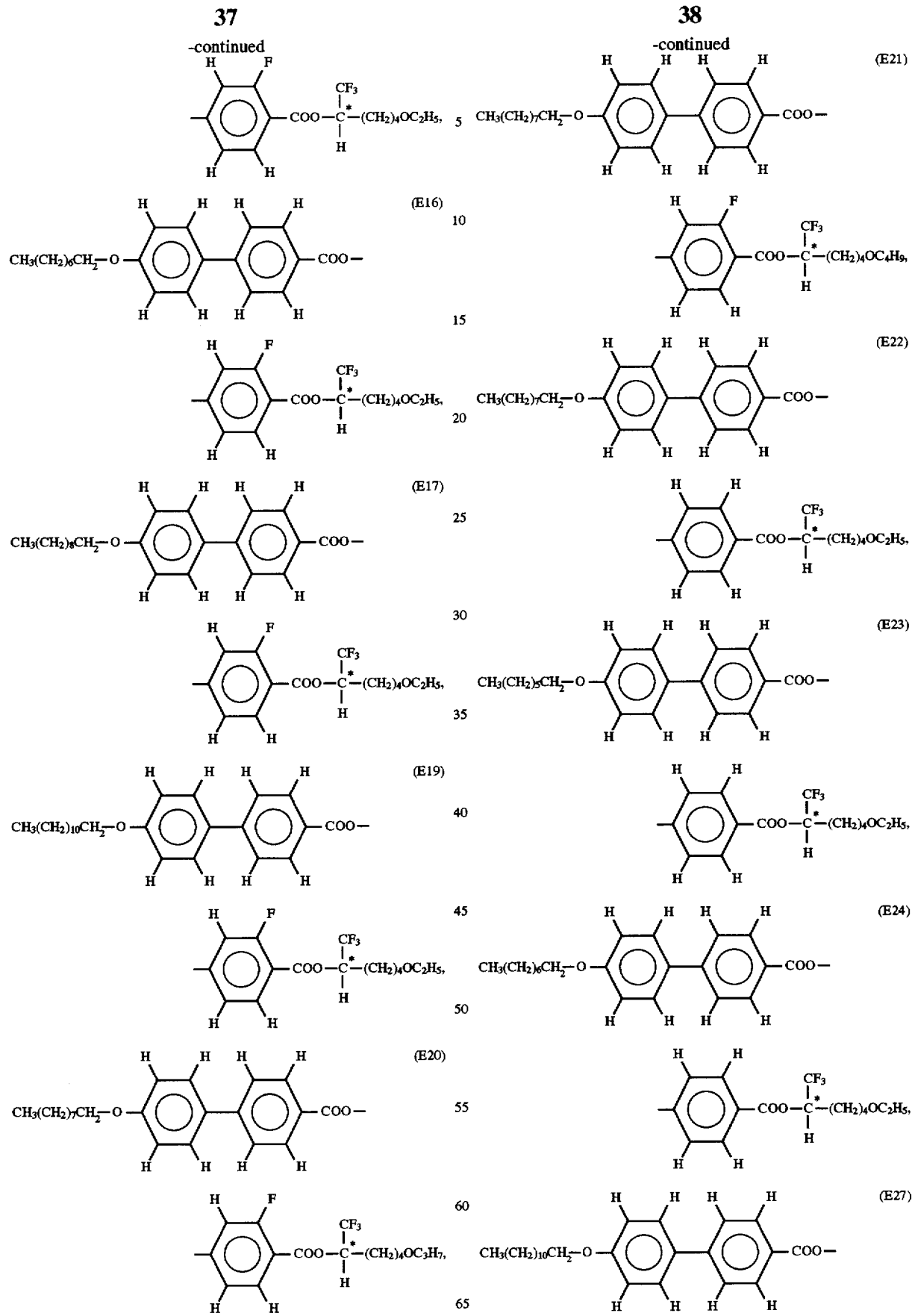

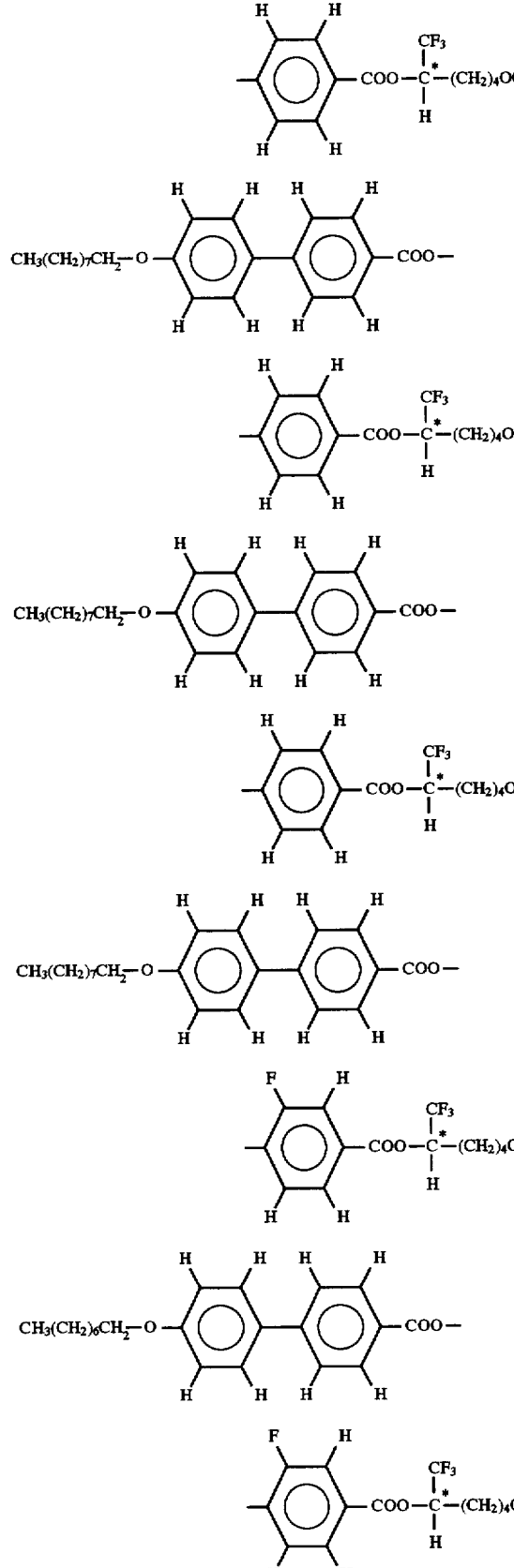

-continued
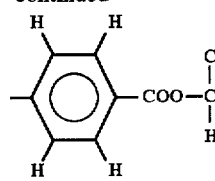
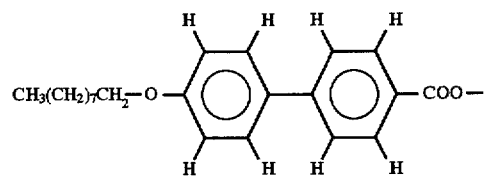 (E37)
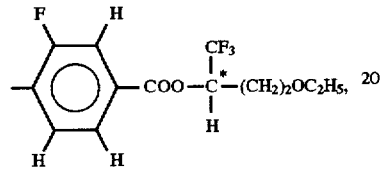 (E38)
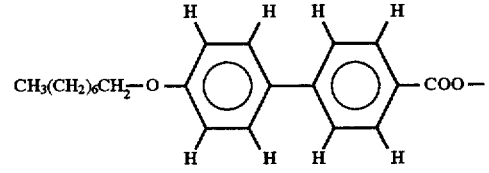
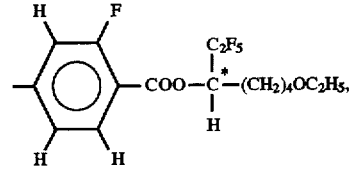
-continued
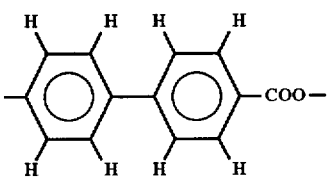 (E39)
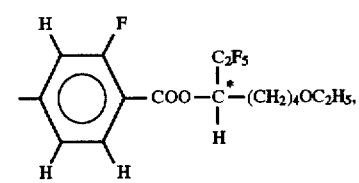
and
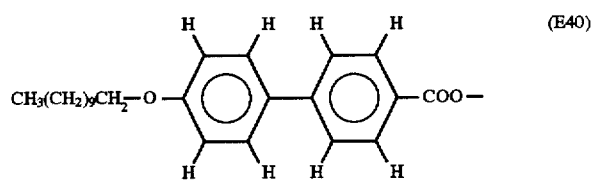 (E40)
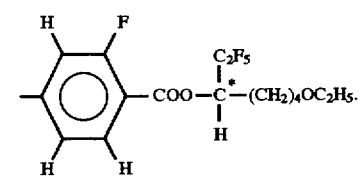
2. A liquid crystal compound having a ferrielectric phase selected from the group consisting of
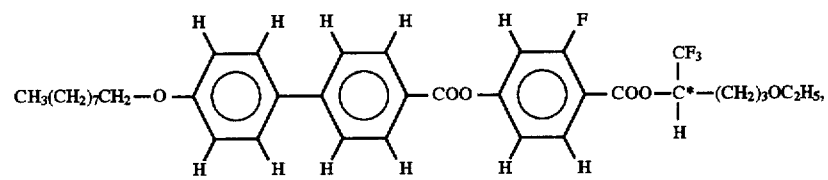 (E1)
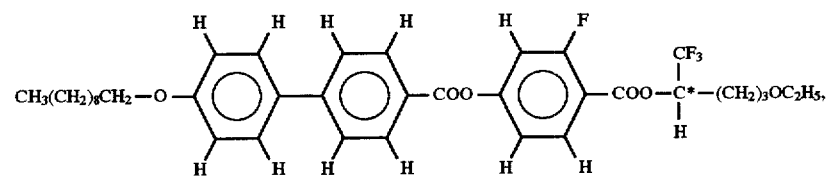 (E2)
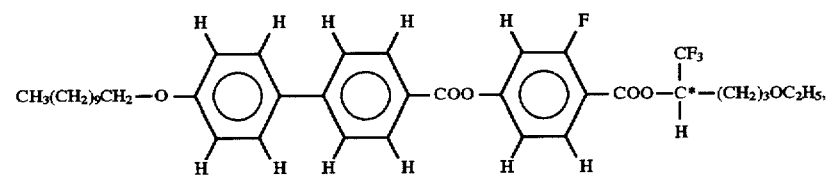 (E3)

-continued
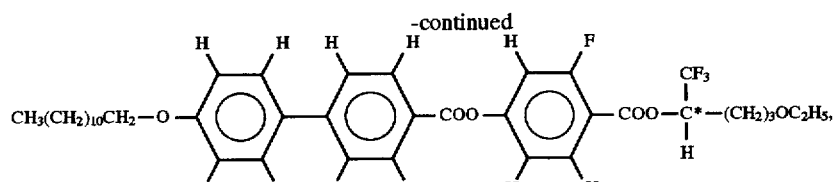 (E4)
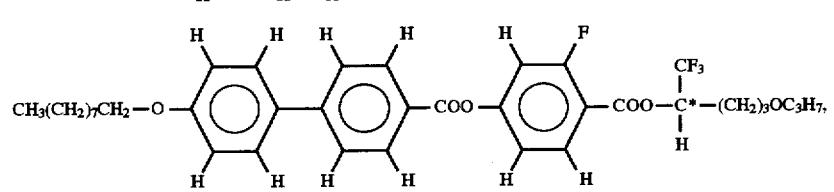 (E5)
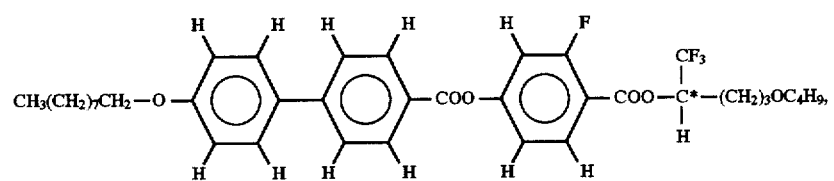 (E6)
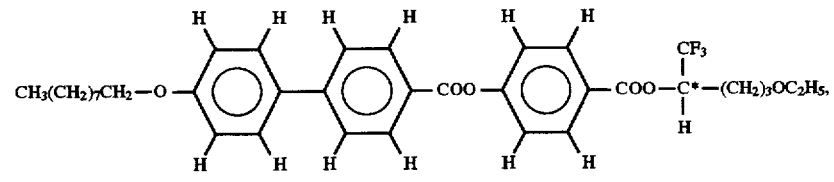 (E7)
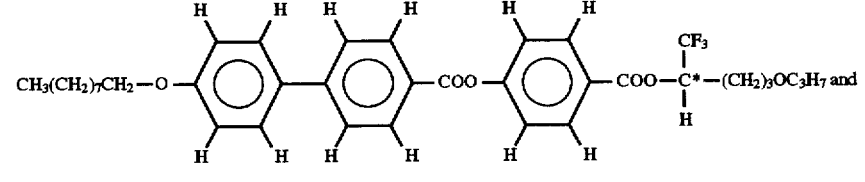 (E8)
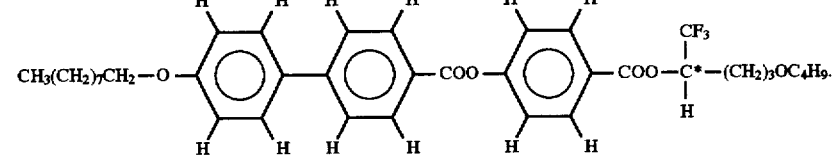 (E9)
3. A liquid crystal compound having a ferrielectric phase selected from the group consisting of
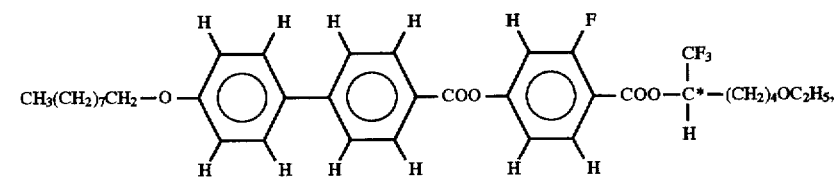 (E13)
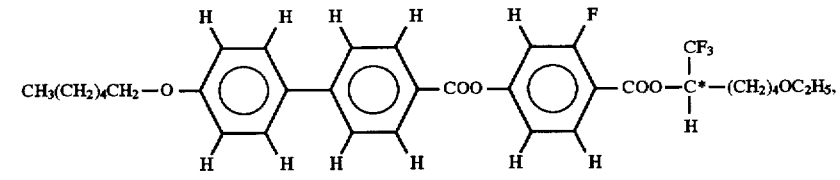 (E14)

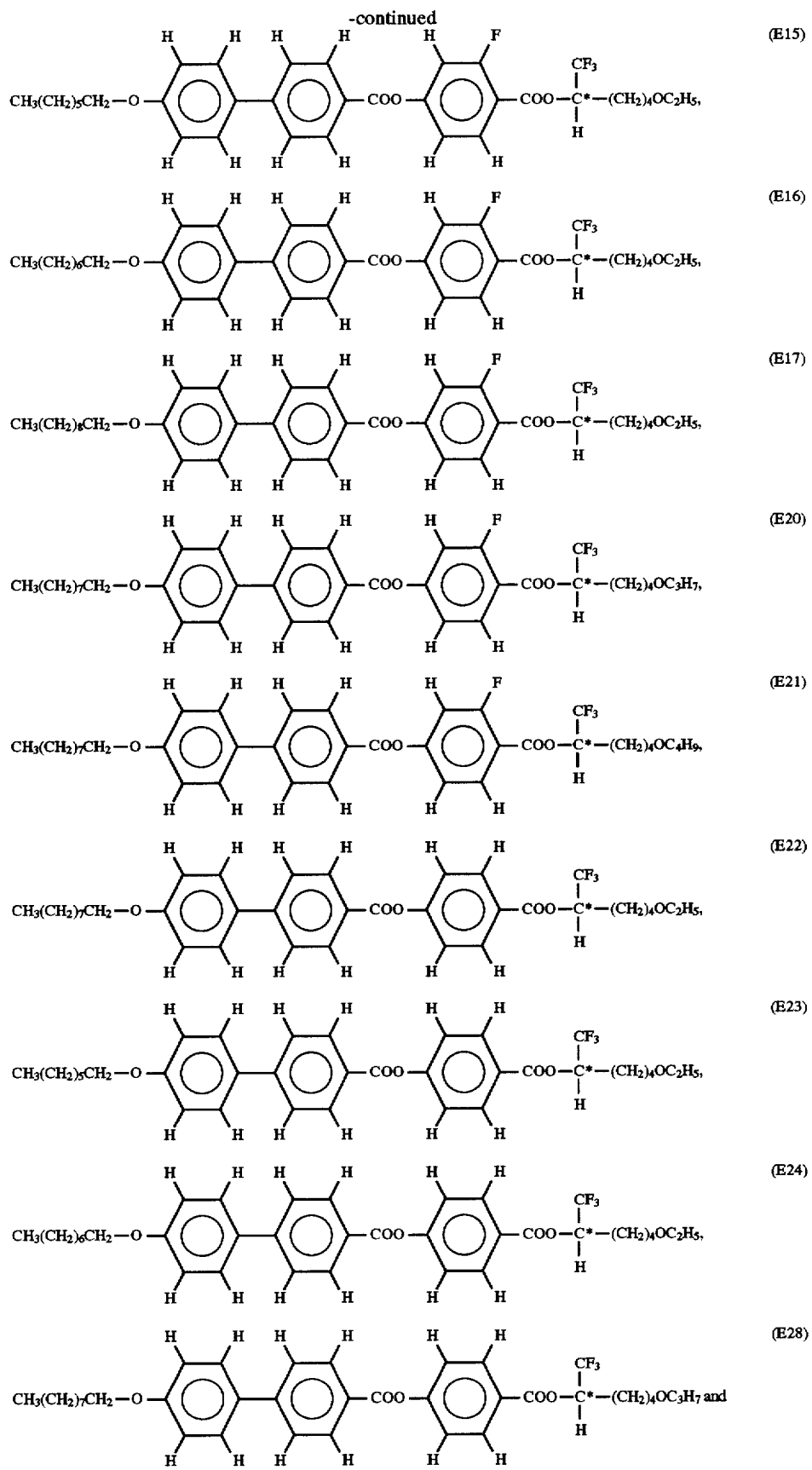

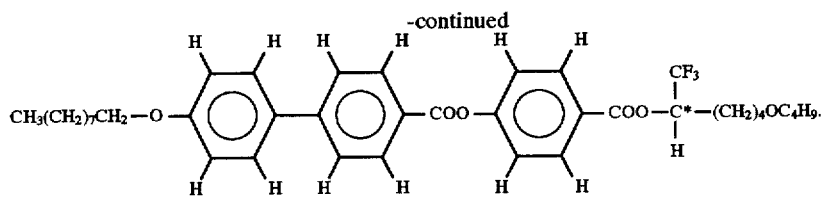
(E29)

4. A liquid crystal compound having a ferrielectric phase selected from the group consisting of

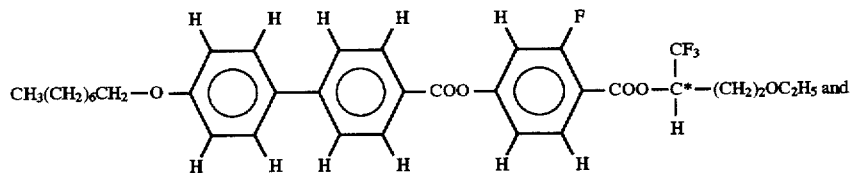
(E35)

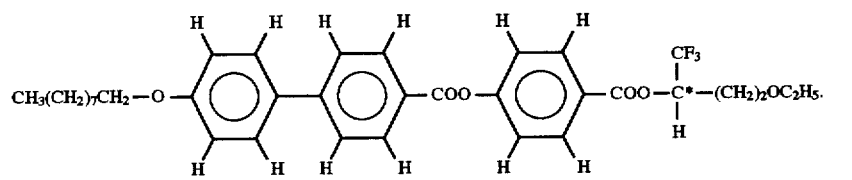
(E36)

5. A ferrielectric liquid crystal composition which contains a liquid crystal compound having a ferrielectric phase as recited in claim 1, has at least a ferrielectric phase in a temperature range of from 0° to 40° C. and has at least a smectic A phase at a temperature higher than that of said ferrielectric phase.

6. A ferrielectric liquid crystal composition which contains a liquid crystal compound having a ferrielectric phase as recited in claim 2, has at least a ferrielectric phase in a temperature range of from 0° to 40° C. and has at least a smectic A phase at a temperature higher than that of said ferrielectric phase.

7. A ferrielectric liquid crystal composition which contains a liquid crystal compound having a ferrielectric phase as recited in claim 3, has at least a ferrielectric phase in a temperature range of from 0° to 40° C. and has at least a smectic A phase at a temperature higher than that of said ferrielectric phase.

8. A ferrielectric liquid crystal composition which contains a liquid crystal compound having a ferrielectric phase as recited in claim 4, has at least a ferrielectric phase in a temperature range of from 0° to 40° C. and has at least a smectic A phase at a temperature higher than that of said ferrielectric phase.

9. The ferrielectric liquid crystal composition of claim 5, wherein the ferrielectric liquid crystal composition further contains a phenyl ester compound of the formula (2),

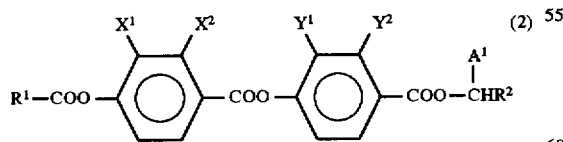
(2)

wherein $R^1$ is a linear alkyl group having 5 to 12 carbon atoms, $R^2$ is a linear alkyl group having 1 to 15 carbon atoms, both of $X^1$ and $X^2$ are hydrogen atoms or one of $X^1$ and $X^2$ is a fluorine atom and the other is a hydrogen atom, both of $Y^1$ and $Y^2$ are hydrogen atoms or one of $Y^1$ and $Y^2$ is a fluorine atom and the other is a hydrogen atom, $A^1$ is a hydrogen atom or —$CH_3$.

10. The ferrielectric liquid crystal composition of claim 9, wherein the phenyl ester compound of the formula (2) has a smectic A phase.

11. The ferrielectric liquid crystal composition of claim 9, wherein $R^1$ is a linear alkyl group having 8 to 12 carbon atoms.

12. The ferrielectric liquid crystal composition of claim 9, wherein $A^1$ is a hydrogen atom and $R^2$ is a linear alkyl group having 2 to 10 carbon atoms.

13. The ferrielectric liquid crystal composition of claim 9, wherein $A^1$ is —$CH_3$ and $R^2$ is an alkyl group having 3 to 8 carbon atoms and the compound of the formula (2) is optically active.

14. The ferrielectric liquid crystal composition of claim 6, wherein the ferrielectric liquid crystal composition further contains a phenyl ester compound of the formula (2),

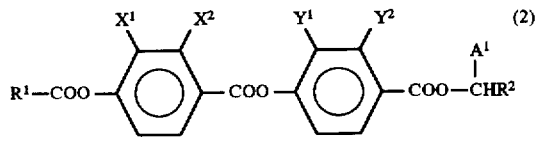
(2)

wherein $R^1$ is a linear alkyl group having 5 to 12 carbon atoms, $R^2$ is a linear alkyl group having 1 to 15 carbon atoms, both of $X^1$ and $X^2$ are hydrogen atoms or one of $X^1$ and $X^2$ is a fluorine atom and the other is a hydrogen atom, both of $Y^1$ and $Y^2$ are hydrogen atoms or one of $Y^1$ and $Y^2$ is a fluorine atom and the other is a hydrogen atom, $A^1$ is a hydrogen atom or —$CH_3$.

15. The ferrielectric liquid crystal composition of claim 14, wherein the phenyl ester compound of the formula (2) has a smectic A phase.

16. The ferrielectric liquid crystal composition of claim 14, wherein $R^1$ is a linear alkyl group having 8 to 12 carbon atoms.

17. The ferrielectric liquid crystal composition of claim 14, wherein $A^1$ is a hydrogen atom and $R^2$ is a linear alkyl group having 2 to 10 carbon atoms.

18. The ferrielectric liquid crystal composition of claim 14, wherein $A^1$ is —$CH_3$ and $R^2$ is an alkyl group having 3 to 8 carbon atoms and the compound of the formula (2) is optically active.

19. The ferrielectric liquid crystal composition of claim 7, wherein the ferrielectric liquid crystal composition further contains a phenyl ester compound of the formula (2),

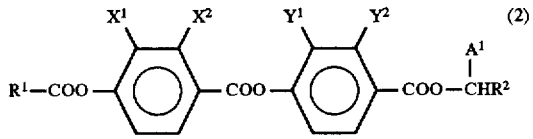

wherein $R^1$ is a linear alkyl group having 5 to 12 carbon atoms, $R^2$ is a linear alkyl group having 1 to 15 carbon atoms, both of $X^1$ and $X^2$ are hydrogen atoms or one of $X^1$ and $X^2$ is a fluorine atom and the other is a hydrogen atom, both of $Y^1$ and $Y^2$ are hydrogen atoms or one of $Y^1$ and $Y^2$ is a fluorine atom and the other is a hydrogen atom, $A^1$ is a hydrogen atom or —$CH_3$.

20. The ferrielectric liquid crystal composition of claim 19, wherein the phenyl ester compound of the formula (2) has a smectic A phase.

21. The ferrielectric liquid crystal composition of claim 19, wherein $R^1$ is a linear alkyl group having 8 to 12 carbon atoms.

22. The ferrielectric liquid crystal composition of claim 19, wherein $A^1$ is a hydrogen atom and $R^2$ is a linear alkyl group having 2 to 10 carbon atoms.

23. The ferrielectric liquid crystal composition of claim 19, wherein $A^1$ is —$CH_3$ and $R^2$ is an alkyl group having 3 to 8 carbon atoms and the compound of the formula (2) is optically active.

24. The ferrielectric liquid crystal composition of claim 8, wherein the ferrielectric liquid crystal composition further contains a phenyl ester compound of the formula (2),

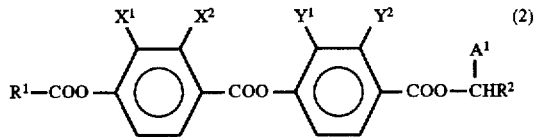

wherein $R^1$ is a linear alkyl group having 5 to 12 carbon atoms, $R^2$ is a linear alkyl group having 1 to 15 carbon atoms, both of $X^1$ and $X^2$ are hydrogen atoms or one of $X^1$ and $X^2$ is a fluorine atom and the other is a hydrogen atom, both of $Y^1$ and $Y^2$ are hydrogen atoms or one of $Y^1$ and $Y^2$ is a fluorine atom and the other is a hydrogen atom, $A^1$ is a hydrogen atom or —$CH_3$.

25. The ferrielectric liquid crystal composition of claim 24, wherein the phenyl ester compound of the formula (2) has a smectic A phase.

26. The ferrielectric liquid crystal composition of claim 24, wherein $R^1$ is a linear alkyl group having 8 to 12 carbon atoms.

27. The ferrielectric liquid crystal composition of claim 24, wherein $A^1$ is a hydrogen atom and $R^2$ is a linear alkyl group having 2 to 10 carbon atoms.

28. The ferrielectric liquid crystal composition of claim 24, wherein $A^1$ is —$CH_3$ and $R^2$ is an alkyl group having 3 to 8 carbon atoms and the compound of the formula (2) is optically active.

* * * * *